(12) United States Patent
Debock et al.

(10) Patent No.: US 12,023,509 B2
(45) Date of Patent: Jul. 2, 2024

(54) ELECTRICAL STIMULATOR FOR PERIPHERAL STIMULATION

(71) Applicant: SPR THERAPEUTICS, INC., Cleveland, OH (US)

(72) Inventors: Matthew G. Debock, Morrisville, NC (US); Joseph W. Boggs, II, Chapel Hill, NC (US); Matthew J. Wunzin, Cleveland, OH (US); Robert B. Strother, Jr., Willoughby Hills, OH (US); Devin Sell, Brecksville, OH (US); Mark R. Stultz, Maple Grove, MN (US); Bradley A. Lewis, Lyndhurst, OH (US)

(73) Assignee: SPR THERAPEUTICS, INC., Cleveland, OH (US)

( * ) Notice: Subject to any disclaimer, the term of this patent is extended or adjusted under 35 U.S.C. 154(b) by 758 days.

(21) Appl. No.: 17/268,248

(22) PCT Filed: Aug. 16, 2019

(86) PCT No.: PCT/US2019/046855
§ 371 (c)(1),
(2) Date: Feb. 12, 2021

(87) PCT Pub. No.: WO2020/037228
PCT Pub. Date: Feb. 20, 2020

(65) Prior Publication Data
US 2021/0316146 A1    Oct. 14, 2021

Related U.S. Application Data

(60) Provisional application No. 62/764,924, filed on Aug. 16, 2018.

(51) Int. Cl.
*A61N 1/375*    (2006.01)
*A61N 1/05*    (2006.01)
(Continued)

(52) U.S. Cl.
CPC ......... *A61N 1/3752* (2013.01); *A61N 1/0529* (2013.01); *A61N 1/36057* (2013.01);
(Continued)

(58) Field of Classification Search
CPC .............. A61N 1/0529; A61N 1/36057; A61N 1/3752; A61N 1/3758; H01R 4/2433; H01R 2201/12
See application file for complete search history.

(56) References Cited

U.S. PATENT DOCUMENTS

| 4,989,617 A | 2/1991 | Memberg et al. |
| 5,167,229 A | 12/1992 | Peckham et al. |

(Continued)

FOREIGN PATENT DOCUMENTS

EP    0382482    8/1990

OTHER PUBLICATIONS

European Search Report for Application 119849776.0, PCT/US2019046855, dated May 6, 2022, 5 pgs., European Patent Office, Germany.

(Continued)

*Primary Examiner* — Christopher A Flory
(74) *Attorney, Agent, or Firm* — McDonald Hopkins LLC

(57) ABSTRACT

A connector assembly includes a base and a detachable cover. Ports on separate sidewalls receive an extension cable and a lead. A blade assembly maintains electrical contact between the cable and the lead, while providing a surface to strip insulation and/or sever the lead. Further, the blade is resilient so as to maintain sufficient contact with the lead when the cover is attached and/or locked to the base.

30 Claims, 17 Drawing Sheets

(51) Int. Cl.
 *A61N 1/36* (2006.01)
 *H01R 4/2433* (2018.01)
(52) U.S. Cl.
 CPC ......... *A61N 1/3758* (2013.01); *H01R 4/2433* (2013.01); *H01R 2201/12* (2013.01)

(56) References Cited

U.S. PATENT DOCUMENTS

| | | |
|---|---|---|
| 5,366,493 A | 11/1994 | Scheiner et al. |
| 5,782,892 A | 7/1998 | Castle et al. |
| 6,845,271 B2 | 1/2005 | Fang et al. |
| 7,376,467 B2 | 5/2008 | Thrope et al. |
| 8,249,713 B2 | 8/2012 | Fang et al. |
| 8,463,383 B2 | 6/2013 | Sakai et al. |
| 8,626,302 B2 | 1/2014 | Bennett et al. |
| 8,700,177 B2 | 4/2014 | Strother et al. |
| 8,788,046 B2 | 7/2014 | Bennett et al. |
| 8,886,337 B2 | 11/2014 | Bennett et al. |
| 8,954,153 B2 | 2/2015 | Boggs, II et al. |
| 8,965,516 B2 | 2/2015 | Bennett et al. |
| 9,248,289 B2 | 2/2016 | Bennett et al. |
| 9,827,412 B2 | 11/2017 | Bennett et al. |
| 9,827,419 B2 | 11/2017 | Boggs, II et al. |
| 9,855,427 B2 | 1/2018 | Bennett et al. |
| 9,887,469 B1 | 2/2018 | King et al. |
| 9,895,530 B2 | 2/2018 | Boggs, II et al. |
| 2002/0038136 A1 | 3/2002 | Zaouali et al. |
| 2003/0199948 A1* | 10/2003 | Kokones ............... A61N 1/0551 607/117 |
| 2011/0257503 A1* | 10/2011 | Mehdizadeh ........ A61N 1/3752 600/393 |
| 2011/0275253 A1 | 11/2011 | D'Hiver et al. |
| 2012/0123502 A1 | 5/2012 | Aghassian et al. |
| 2013/0018445 A1 | 1/2013 | Sakai et al. |
| 2014/0046416 A1* | 2/2014 | Bennett ............... A61N 1/36071 607/116 |
| 2016/0099508 A1 | 4/2016 | Ozaki |
| 2016/0218444 A1* | 7/2016 | King, Jr ............... H01R 4/2454 |
| 2016/0250466 A1 | 9/2016 | Boggs et al. |
| 2017/0332924 A1* | 11/2017 | Mehdizadeh ............ A61B 5/24 |

OTHER PUBLICATIONS

Patent Cooperation Treaty (PCT), International Search Report and Written Opinion for Application PCT/US2019/046855 filed Aug. 16, 2019, dated Oct. 28, 2019, International Searching Authority, US.

* cited by examiner

ELECTRICAL STIMULATOR FOR PERIPHERAL STIMULATION

CROSS-REFERENCE TO RELATED APPLICATION

This application is a 35 U.S.C. § 371 national stage application of PCT Application No. PCT/US2019/046855 filed on Aug. 16, 2019, entitled "ELECTRICAL STIMULATOR FOR PERIPHERAL STIMULATION," which claims priority to United States Provisional Patent Application Serial No. 62/764,924 filed on Aug. 16, 2018. The disclosure of these applications, along with any other United States Patents and United States Patent Publications identified in this specification, are hereby incorporated by reference.

FIELD OF USE

The present disclosure generally relates to an electrical stimulator system and, more particularly, a lead connector for use with such a system.

BACKGROUND

Neurostimulation and brain stimulation can provide functional and/or therapeutic outcomes. While existing systems and methods provide benefits to individuals requiring neurostimulation, many quality of life issues still remain. For example, existing systems are performed solely in a clinical setting under the supervision of a clinician limiting the applicable uses and the time available for stimulation. Furthermore, the controllers utilized in these clinical settings, by today's standards, are relatively large and awkward to manipulate and transport.

There exist both external and implantable devices for providing neurostimulation in diverse therapeutic and functional restoration indications. These neurostimulators are able to provide treatment therapy to individual portions of the body. The operation of these devices typically includes use of an electrode placed either on the external surface of the skin and/or a surgically implanted electrode. In the case of external neurostimulators, surface electrodes and/or percutaneous lead(s) having one or more electrodes are used to deliver electrical stimulation to select portion(s) of the patient's body.

For example, transcutaneous electrical nerve stimulation ("TENS") is delivered through electrodes placed on the skin surface, but has not achieved widespread use due to discomfort of the therapy, muscle fatigue, and the limited efficacy. TENS is similar to electrical muscle stimulation, although the latter is intended for stimulating muscles rather than nerves.

Several clinical and technical issues associated with surface electrical stimulation have prevented it from becoming a widely accepted treatment method. First, stimulation of cutaneous pain receptors cannot be avoided resulting in stimulation-induced pain that limits patient tolerance and compliance. Second, electrical stimulation is delivered at a relatively high frequency to prevent stimulation-induced pain, which leads to early onset of muscle fatigue. Third, it is difficult to stimulate deep nerves with surface electrodes without stimulating overlying, more superficial nerves resulting in unwanted stimulation. Further still, clinical skill and intensive patient training is required to place surface electrodes reliably on a daily basis and adjust stimulation parameters to provide optimal treatment. The required daily maintenance and adjustment of a surface electrical stimulation system is a major burden on both patient and caregiver.

A number of previous systems for spinal cord stimulation (e.g., at the dorsal root ganglion) and/or other deep tissue stimulation require surgical implantation of electrodes and/or other devices for delivering the therapy. These therapies necessarily incur the cost and medical risks associated with invasive surgical procedures, and they may restrict the mobility of the patient, both in terms of the surgical procedure itself and, in some cases, in the post-operative activities an ambulatory patient may wish to engage in while in his or her home environment.

U.S. Pat. No. 7,376,467 discloses a neuromuscular stimulation assembly including a steerable introducer defining an interior lumen that shields the electrode from contact with tissue during insertion. Electrodes suitable for this assembly may be transcutaneous or percutaneous. The assembly includes a carrier, adhesively held to the patient, having an electronics pod for generating the desired electrical current patterns and an optional power input bay to enable changing the batteries for the assembly. Electrical connections between the electrodes and the power source are established via troughs that are integrally formed on the pod.

U.S. Pat. No. 8,700,177 describes a system and method involving the use of an adhesive patch with a mounting structure directly mated to an electrical stimulation device. A percutaneous electrode is electrically coupled to the stimulation device. The device has a low profile and may be controlled wirelessly or by way of a plugged connection. A rechargeable battery powers the device, which may be inductively charged.

SUMMARY

A compact lead connector system for use with electrical nerve stimulation devices is disclosed. In its most fundamental form, the connector comprises an electrically passive base with a detachable cover. Separate receiving ports are provided in separate facings of the connector to receive the lead and the extension cable. A blade-like connector establishes and maintains electrical contact between the lead and the cable, while also providing the ability to strip insulation and sever excess or unwanted portions of the lead. Additional aspects of the system include additional extension cable adapters that vary in diameter and/or other features, while an unlocking tool facilitates disconnection of the cover from the base. Also, a connector cradle may be provided to retain the connector and keep it affixed to the patient.

Specific embodiments of the present teachings may include any combination of the following features:
- a base having a cable port positioned within a first sidewall and a lead port positioned within a second sidewall;
- a cover, selectively attachable to the base so as to define an internal cavity, the cover having a cable securing boss that is positioned proximate to the cable port when the cover is attached to the base;
- a contact blade, held between the cover and the base when the cover is attached to the base, the contact blade having a flattened angled portion and an extension portion protruding into the internal cavity so as provide electrical contact between a cable inserted through the cable port and a lead inserted through the lead port;
- wherein the flattened angled portion is L-shaped;
- wherein the cable is welded to the angled portion;

wherein the extension portion includes a plurality of resilient members, with at least one of the plurality of resilient members including a cutting edge at a terminal edge disposed within the internal cavity, said cutting edge stripping or severing the lead when the cover abuts or is attached to the base;

wherein the plurality of resilient members consists of two generally parallel members;

wherein the two generally parallel members collectively define an S-shape;

wherein a first of the two generally parallel members is offset so as to extend into the internal cavity at a different axial height, relative to the flattened angled portion, in comparison to a second of the two generally parallel members;

wherein all of the plurality of resilient members each have a cutting edge;

wherein the plurality of resilient members includes at least three generally parallel members;

wherein all of the parallel members are axially offset relative to one another so as to extend into the internal cavity at a different axial heights relative to the flattened angled portion;

wherein the plurality of resilient members have a serpentine shape;

wherein the plurality of resilient members form an initial angle, relative to the flattened angled portion of between 45° to 75°;

wherein the contact blade is attached to the cover;

wherein a hinge connects the cover to the base;

wherein the first sidewall is directly adjacent to the second sidewall;

wherein the contact blade is metallic;

wherein the cover includes an axially-aligned securing post that abuts the base and secures the lead within the internal cavity when the cover is attached to the base;

wherein the base includes a guide channel on a bottom panel of the base, the guide channel receiving the lead within the internal cavity;

wherein the cover includes at least one ramped clamp and the base includes a cooperating catchment shaped to receive the clamp so that the clamp attaches and locks the cover to the base;

wherein at least one of the cable port and the lead port has a funnel-shape;

wherein the cover includes a cable boss so that, when the cover is attached to the base, the cable boss encloses a portion of the cable port;

at least one extension cable;

wherein a plurality of extension cables connected in series and having a progressively larger diameter relative to the cable received within the cable port;

wherein a plurality of extension cables connected in series by way of a magnetic and/or breakaway connection;

an unlocking tool having a plurality of bosses cooperating with corresponding apertures in the cover or the base to release a clamp that attaches and locks the cover to the base;

wherein the cover includes at least one ramped clamp and the base includes a cooperating catchment shaped to receive the clamp so that the clamp attaches and locks the cover to the base and wherein the plurality of bosses release the clamp from the catchment when inserted through the corresponding apertures in the cover;

a mounting cradle having a pair of side walls sized to receive and secure the connector and a cradle base;

wherein the base comprises an adhesive patch;

the cradle further comprising an end wall connected to the pair of side walls;

wherein the connector includes a feature for snap-fitting to the cradle; and wherein the feature comprises laterally extending wings on opposing sidewalls of the base of the connector.

These and other features and advantages of the present teachings are set forth in the following specification, drawings and claims.

BRIEF DESCRIPTION OF THE DRAWINGS

These and other features, aspects and advantages of the present disclosure are better understood when the following detailed description is read with reference to the accompanying drawings, in which:

FIG. 1A is a perspective view of the lead connector showing the funnel-shaped port positioned on an elongated side wall of the lead connector, while FIG. 1B is an opposing perspective view relative to FIG. 1A highlighting the opposing elongated side wall visible and some of the features along the edge of the partially ajar lid of the lead connector. FIG. 1C is a side plan view of the elongated side wall visible in FIG. 1B. FIG. 1D is a side plan view taken along the elongated side wall visible in FIG. 1A, highlighting the port through which the lead is received and which includes a funnel shaped opening and an aperture connecting with the internal cavity of the connector itself. FIG. 1E is a side plan view taken along the narrow, front side wall of FIG. 1A, highlighting the opening through which the cable may be inserted.

FIGS. 2D, 2E, 2F and 2G are an isolated perspectives of various embodiments of the attachment blade (with FIG. 2D being the blade shown in FIG. 2A), while FIG. 2F is a cross sectional side view of the blade shown in FIG. 2E.

FIG. 5A is a side plan view taken along the narrow, front side wall of FIG. 4B, highlighting the opening through which the lead may be inserted but with the plug omitted in this view. FIG. 5B is a side plan view taken along the elongated side wall encompassing the stimulator extension cable of FIG. 4B. Note that the stimulator extension cable is shown in cross section, thereby omitting the plug in this view. FIG. 5C is a top plan view of FIG. 5A, while FIG. 5D is a corresponding bottom view.

FIG. 6A is a perspective view of an unlocking device which may be used with the lead connector along the facing illustrated in FIG. 5D, while

FIG. 10A is a cross sectional, lengthwise view of a lead wire illustrating how multiple conductive wire strands are encased within an insulative coating, while

FIG. 11A represents various, spaced apart points on the same leads, whereas FIG. 11B shows a time-lapse effect of one blade.

DETAILED DESCRIPTION

Figure 1A:
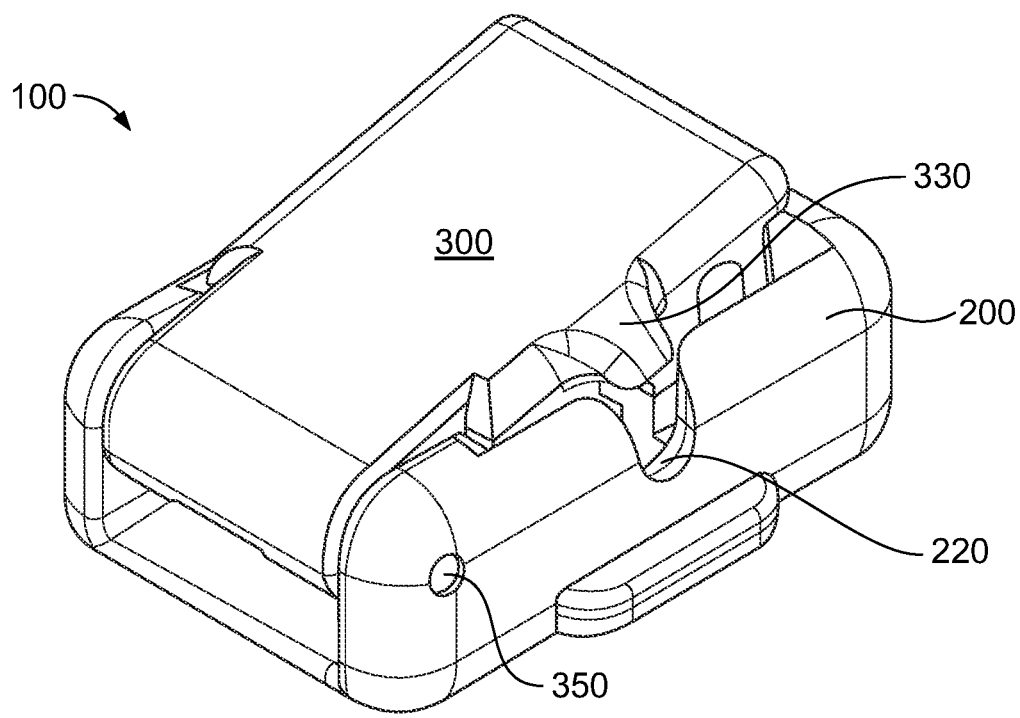
FIGS. 1A through 1E are various views of the lead connector, in closed but unlocked state, according to various aspects of the invention.
Figure 1B:
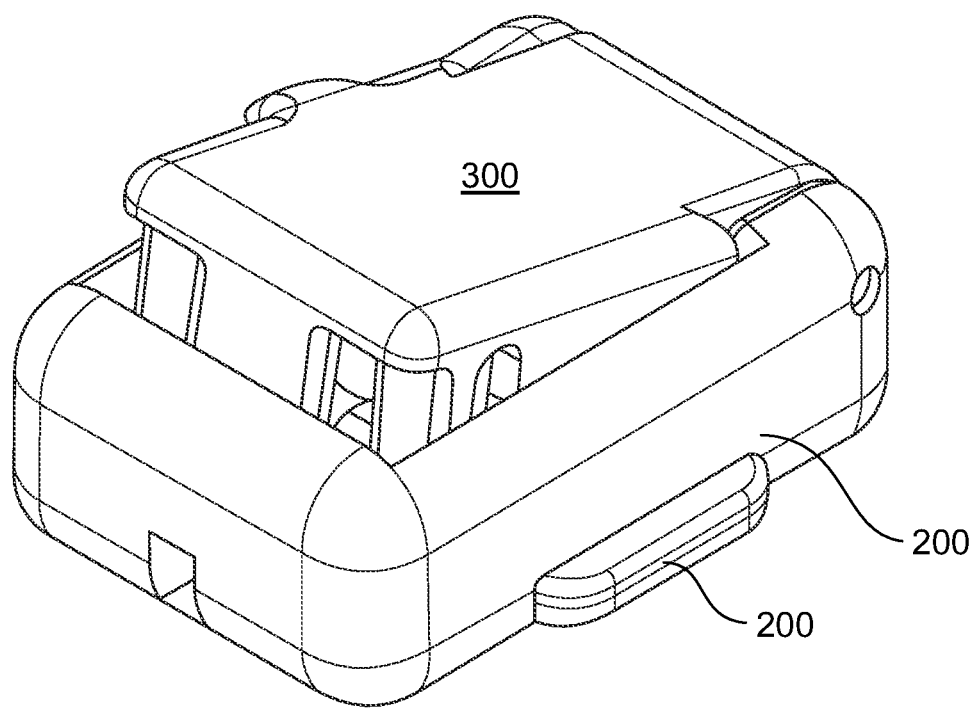
Figure 1C:
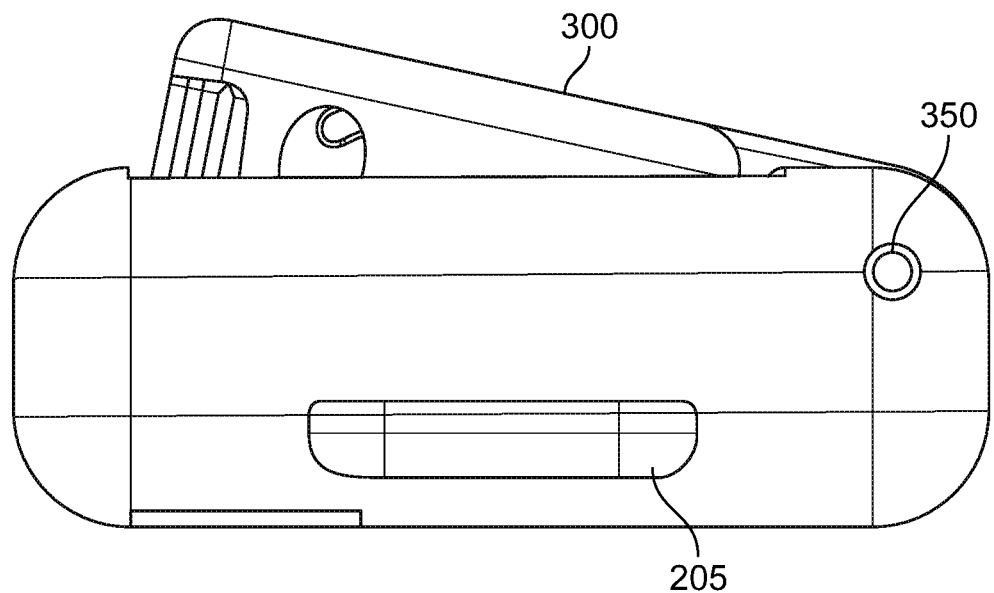
Figure 1D:
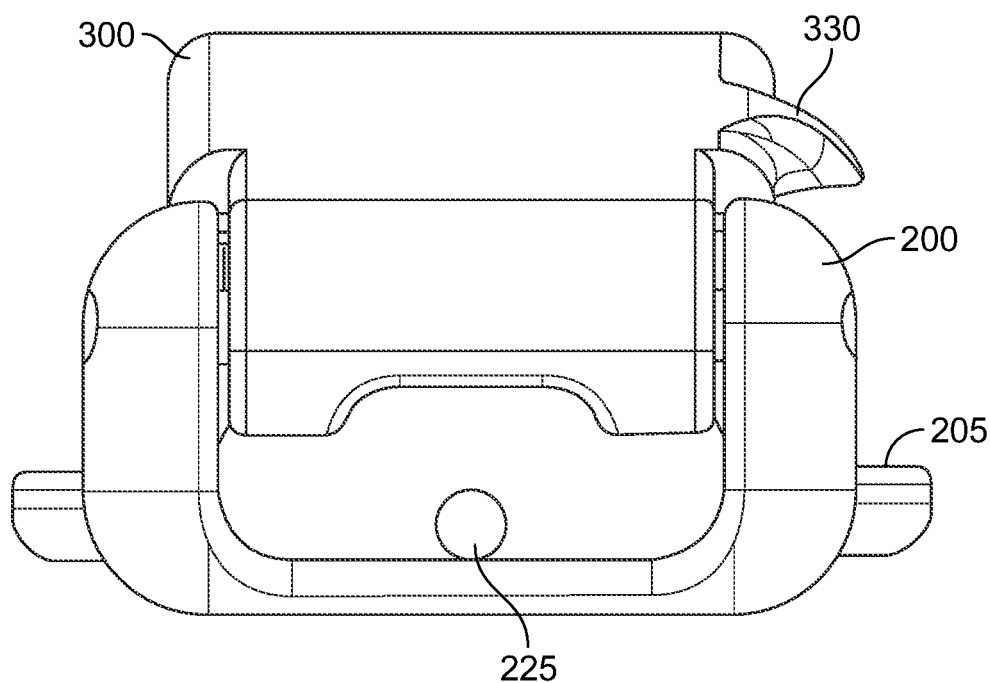
Figure 1E:
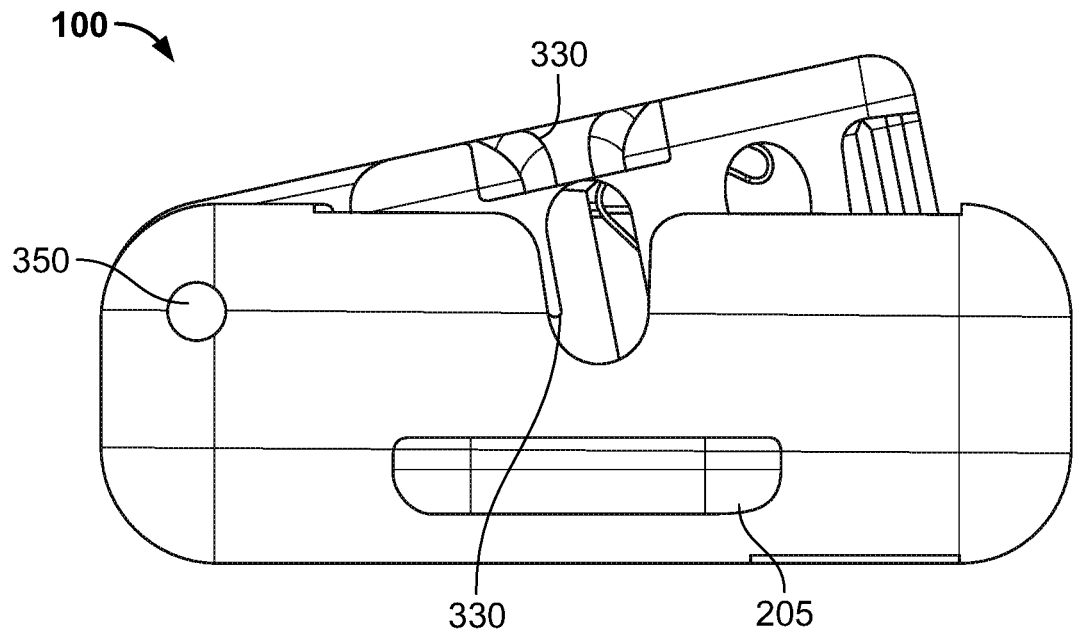

Reference will now be made in detail to exemplary embodiments of the present teachings, examples of which are illustrated in the accompanying drawings. It is to be understood that other embodiments may be utilized and structural and functional changes may be made without departing from the respective scope of the present teachings. Moreover, features of the various embodiments may be combined or altered in any combination without departing from the scope of the present teachings. As such, the following description is presented by way of illustration only and should not limit in any way the various alternatives and modifications that may be made to the illustrated embodiments and still be within the spirit and scope of the present teachings.

As noted above, previous neurostimulation and neuromodulation systems have inherent weaknesses that the present invention addresses and overcomes. For example, these weaknesses may include difficulty using the stimulator while it is mounted on difficult to reach position of the body, a position on the body that is subject to frequent movement, including, without limitation the patient's arm, back, leg, head, shoulder, etc. Further, it may be difficult for a clinician to couple the stimulator with the lead, including, without limitation a fine-wire lead, and particularly an open coil lead, and may be difficult for the clinician to work with the system while on the patient body. Further still, other weaknesses may be the inherent difficulty with operating the system while it is adhered to the body, the difficulty replacing bandages without fear of dislodging the electrode, and discomfort due to system size and shape. Certain embodiments of the present teachings overcome these weaknesses and provide additional advantages, as will be recognized by persons of skill in this field.

The lead connector contemplated herein is useful for establishing electrical communication between one or more electrodes and a signal generator in neurostimulators and other, similar stimulation devices. Non-limiting examples of such devices, as well as systems and methods of operation and use of such devices and systems, can be found in U.S. Pat. Nos. 6,845,271; 8,249,713; 8,463,383; 8,626,302; 8,788,046; 8,886,337; 8,954,153; 8,965,516; 9,248,289; 9,827,412; 9,855,427; and 9,895,530; all of which are incorporated by reference herein.

There is a clinical need for a device that delivers therapeutic electrical stimulation (e.g. peripheral nerve stimulation (PNS)) to a nerve (e.g. peripheral nerve) innervating the region of pain to provide pain relief. The device may deliver stimulation to the nerve transmitting the pain signal or it may deliver stimulation to a nerve, which is not transmitting the pain signal, but when stimulation is delivered, a condition or symptom, such as pain, may be relieved or improved and/or function may be improved or restored. The device may deliver pain-relieving or function-restoring peripheral nerve stimulation in a variety of settings including chronic, acute, post-surgical, post-traumatic, and intermittent pain and/or loss of function, and other conditions (e.g., other types of pain and/or functional loss), as well as across a range of anatomical regions, including but not limited to limbs (e.g., arms, legs, etc.), extremities (e.g., hands, feet, fingers, toes, etc.), joints (e.g., hips, knees, shoulders, elbows, ankles, wrists, etc.), back, neck, head, face, and other regions. A percutaneous electrical stimulator system may include an electrode percutaneously insertable into a patient, an adhesive bandage at least partially securing a proximal end of the electrode protruding from the patient, a lead connector, fixed to the proximal end of the electrode, a patient cable or cables detachably connected to the lead connector, and a stimulator connected to the patient cable and forming an electrical connection between the stimulator and the electrode to deliver therapeutic stimulation.

As used herein, the term lead includes reference to the wire, cable, or other member that establishes connection between the electrode(s) and the stimulator. Often, the size/diameter of the lead, which may penetrate the skin, is different (and usually much smaller) than the size/diameter of the external connection cables, which are designed for handling by the patient, clinician, and others. Non-limiting examples of leads appropriate for use with the inventive connector system can be found in U.S. Pat. Nos. 4,989,617; 5,167,229; and 5,366,493, as well as United States Patent Publication 2013/0018445, all of which are incorporated by reference.

Generally speaking, the connector can be used on any thin wire leads, and particularly those wrapped in protective insulation. Such thin wires may have a diameter of less than 1.25 mm and, more preferably, less than 0.6 mm. The wire within the insulation and/or forming the distal electrode(s) can be formed in a spiral or helix shape, while the distal end is implanted by a hypodermic needle or surgical procedure and connected to stimulators which generate the simulation profiles/therapies noted above. Further, the electrode may have a generally coiled or helical structure, rather than a smooth cylinder. However, the present teachings are not limited to this structure of lead. Any appropriate configuration may be utilized without departing from the present teachings.

It is desirable for the lead to have a relatively small diameter, especially to the extent it connects to an electrode that is implanted within and/or beneath the skin. By providing a lead connector that allows attachment of thicker, more sturdy cable extensions (also referred to as pigtails), the amount of exposed, the robustness of the device/system can be increased and/or less robust wiring (e.g., the lead wire) can be reduced or eliminated entirely.

The system further contemplates the use of additional cable extensions. These cables may increase in diameter by steps of greater than 0.75 mm. Additional connections can be made by way of magnetic and/or spring-loaded/tensioned connections, similar to those described in U.S. Pat. No. 9,827,419, which is also incorporated by reference. As the diameter of the pigtails is increased, it becomes possible to incorporate one or two-pronged plugs, including arrangements with opposing polarities, in order to allow for use with and connection to a wider variety of stimulators, pulse generators, and other similar devices. In certain embodiments, the pigtail(s) may consist of 26 gauge stranded copper wire wrapped in PVC insulation.

The connector 100 is shown in FIGS. 1A though 5D. Connector 100 comprises a base unit 200 and a cover member 300. Base 200 and cover 300 may be rotatably and/or permanently attached to one another by hinge or axle 350. By keeping the pieces attached, it ensures quick and reliable alignment of the cable port 220, as described below.

Base 200 include a plurality of sidewalls 201 and a bottom panel 203. When the cover 300 is fitted in place, an internal cavity 204 is formed. Both the extension or pigtail cable 20 and the lead are received into cavity 204 by way of separate ports 220, 225. Additionally, unlocking apertures 202 allow a tool to penetrate into cavity 204 so as to release the locking clamps 310 from their cooperating catchment 210.

Port 220 is positioned in one of the sidewalls 201. Port 220 may be an aperture or U-shaped indentation which forms an aperture when cover 300 is fitted and closed/sealed onto the body 200. In either instance, the outer facing of port 220 has a funnel-like shape so as to facilitate receipt of the cable 20.

The cable 20 may be permanently affixed to the connector 100, especially via the blade component 400 (described below) so that the only connection made by the user will be between the lead and the connector 100. The cable 20 (extension or pigtail cable) may be affixed by soldering, brazing, welding or other appropriate method of electrically and mechanically mating to the connector and especially to the blade(s) of the connector. Additional supporting mechanical connections directly to the base 200 or cover 300 may also be incorporated, such as the use of an additional wire cover or component that may provide additional strain relief to the cable and reduce the risk of fracture during repeated use.

One or more catchments 211 rise axially from the bottom panel 203. A guide 211, possibly in the form of a smooth or contoured facing proximate to the port 220, facilitates alignment of the cable 20 within the cavity 204. Blade 400 may abut with or even be fitted proximate to the catchment 210, as will be described in greater detail below.

Figure 2A:
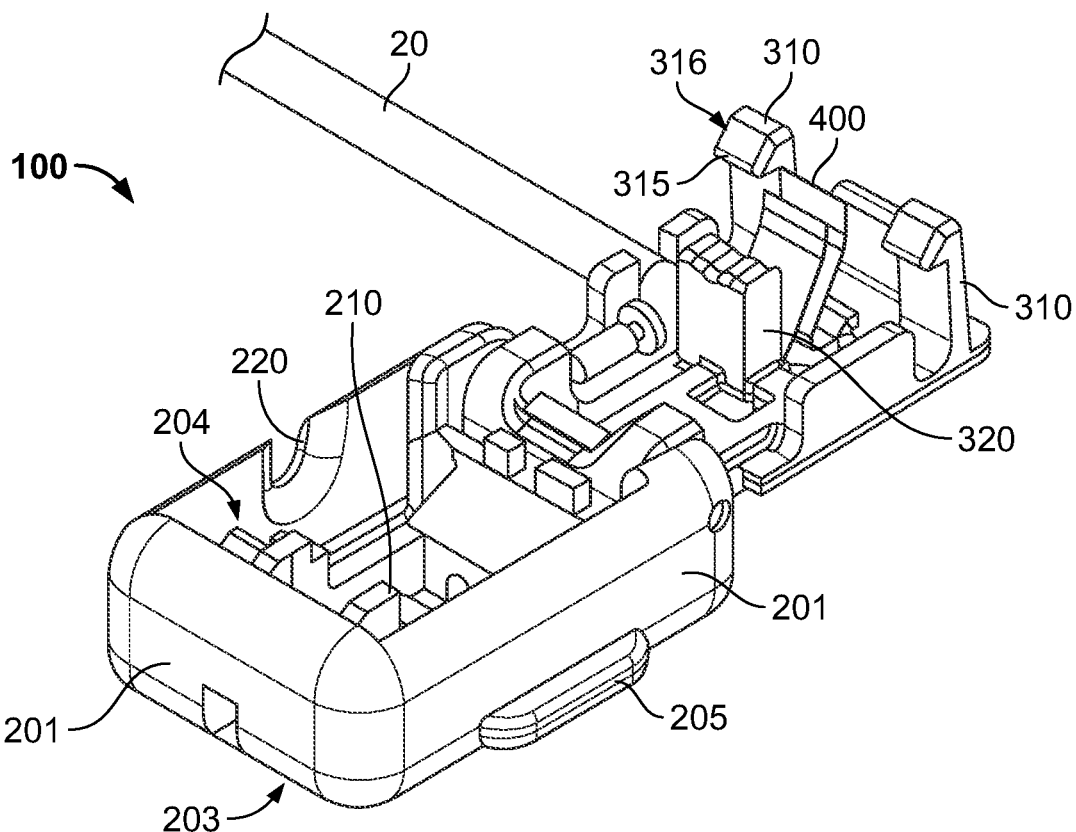
FIG. 2A is a perspective view, similar to that of FIG. 1B, showing the lead connector in a completely opened state, with the stimulator extension cable (with the distal plug not shown) entering and connected to the lead connector itself although, in actual use, the connector need not be placed into this completely opened state.
Figure 2B:
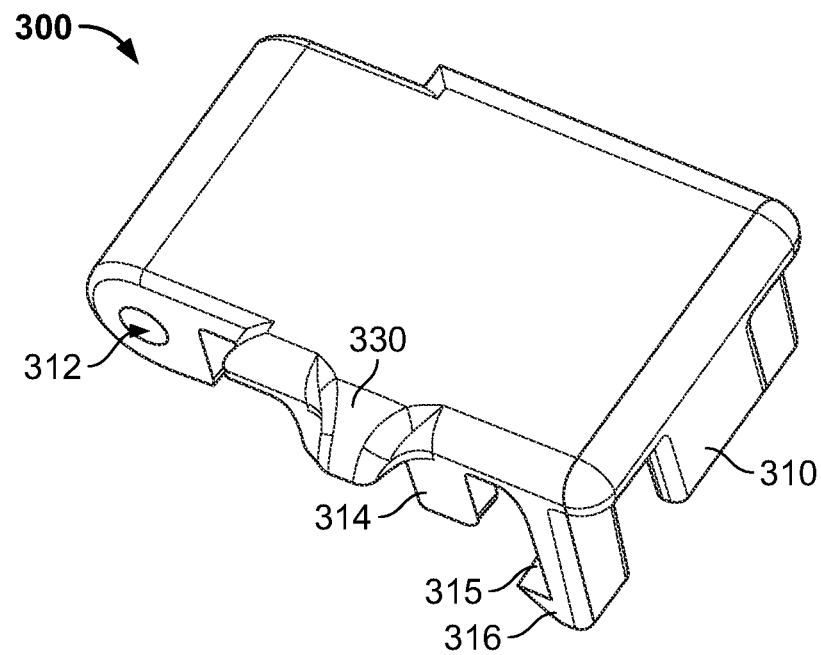
FIG. 2B is an isolated perspective view of the top side of the cover of the lead connector (as shown in FIG. 2A).
Figure 2C:
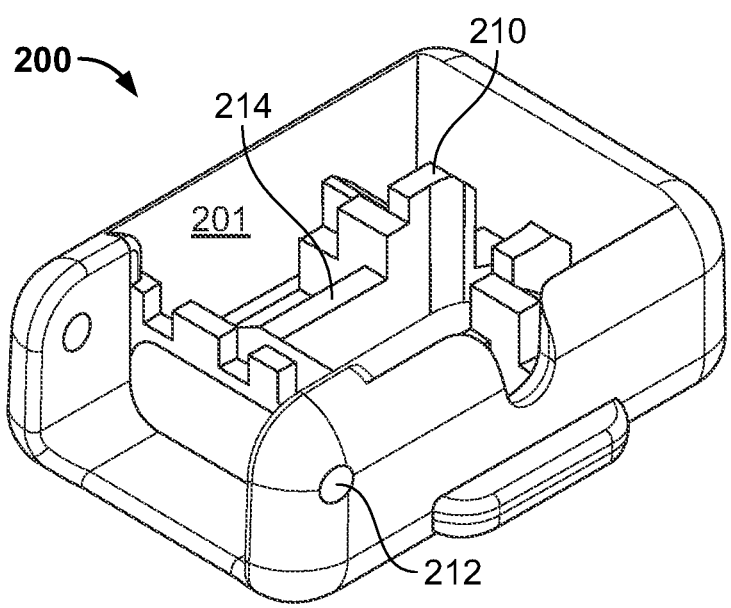
FIG. 2C is an isolated perspective view of the features of the base of the lead connector (as shown in FIG. 2A) along its inner cavity.

One of the sidewalls 201 may be partially or completely removed so as to accommodate hinge 350. As is best seen in FIG. 2C, aligned apertures 212 receive a pin or rivet (not shown in 2C) which serves as hinge 350. A corresponding aperture 312 in the cover 300 (seen in FIG. 2B) completes the connection.

A guide channel 213 may also be formed on bottom panel 203 to facilitate receipt and connection of the lead within the cavity 204. Such guide 213 cooperates with lead port 225, which also has an oval or circular funnel shape so as to impart a frusto-conical facing, although any shape and size aperture could be employed. Optionally, barbs or friction members could be formed in or near the port 225 and/or guide 213 to secure the lead after it has been inserted into cavity 204. Additionally, a securing post 320 is formed on the cover 300 and extends axially downward into cavity 204 when cover 300 is locked to the base 200, with post 320 restraining the lead to facilitate further connection and action of the blade(s) 400.

One or more optional support ribs 214 can be formed within the cavity 204. Ribs 214 may rise from the bottom panel 203 and/or connect with one or more of the sidewalls 201. Ribs 214 provide structural support to the overall connector 100 by providing lateral, transverse, and/or axial support, particularly when the cover 300 is clamped in a closed position.

Blade 400 is received in cavity 204 and held on and/or between the base 200 and/or cover 300. Connection may be made by snap fitting, screws, adhesive, or other appropriate means. Blade 400 provides the electrical connection between the cable 20 and the lead, so that its shape will conform to the position of the ports 220, 225.

Figure 2D:
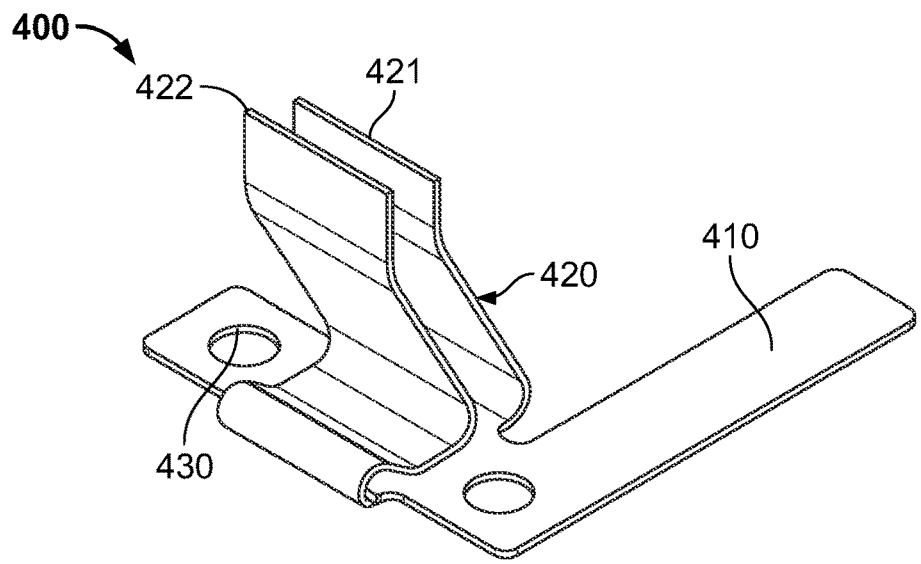

As shown in FIG. 2D, blade 400 includes an angled, flat base 410 and an axial extension 420. While reference is made to the connecting blade 400, it will be understood that the blade 400 is a mechanical and electrical connector, and can include any physical implementation of arms or attaching elements (i.e., extension(s) 420) extending out from a planar contact element imparted with a shape that conforms to and spans the physical separation between ports 220, 225 (i.e., angled, flat base 410). Apertures 430 can accommodate screws or fasteners to ensure the blade 400 remains affixed to cover 300, although it may be possible to configure blade 400 to be carried on the base 200. The apertures may also be designed in conjunction with the connector lid or base such that the blade can be press fit directly to the lid or base.

Flat base 410 may be L-shaped, with the extension 420 arising from one end and the contact point 412 formed to make electrical connection with cable 20. In some embodiments, that electrical connection may include welding, while other embodiments contemplate an abutting relationship in which blade 400 is biased against one or more cooperating, exposed contact points on or near the distal end of the cable 20.

Extension 420 preferably includes a pair bent or serpentine members 421, 422. The edge of member 421 can be formed to have an angle, so as to engage and hold the lead, thereby imparting an S-shape to allow the members to flex slightly. The terminal edge of member 422 is offset from the terminal edge of member 421 a sufficient distance to strip insulation from the distal end of the lead. The members 421, 422 are also sized to cooperate with the channel 213 (if present) and/or bottom panel 203 (along its facing forming the cavity 204) proximate to the port 225. In some aspects, when the cover 300 is locked (i.e., so that the capture edge 315 of clamps 310 engage the catchment 210, rather than being merely closed—as in FIGS. 1A through 1E, where the ramp portion 316 of clamps 310 merely rests on and abuts catchment 210 without edge 315 snapping-fit thereunder), sharpened edges at the distal end of member 421 and/or member 422 is/are capable of severing the lead. When the cover 300 is closed, these edges can potentially strip the insulation. In other embodiments, the positioning of blade 400 can be adjusted so that severing or stripping can be achieved only when the cover 300 is locked or only when the cover is closed.

There are particular challenges in establishing connection to an open-coil, small diameter lead, especially with an insulating coating which contains the metallic wire of the lead. For example, it may be necessary to connect at various locations along the length of the lead (e.g., to optimize the length of lead outside of the skin or body), and it can be difficult to reliably form a connection to the metal wire encapsulated in insulation. Further still, it is important to avoid damaging the lead in a manner that causes the connection to fail, and aligning the complex geometry and structure of an open-coil design is difficult because the lead/wire can be crushed or displaced in a variety of ways that may impede a reliable electrical and mechanical connection. Finally, in a general sense, managing, controlling and manipulating a very small, very flexible lead wire especially when being manipulated in a clinical scenario where gloves may impede the dexterity of the persons handling the lead and connector cannot be overlooked.

Numerous design features described herein which may work synergistically to accomplish a reliable, consistent electrical and mechanical connection with an open coil lead. For example, the use of a funnel shape and supporting structures within the base of the connector may aid in guiding a small, flexible and difficult to control lead wire into the correct location in line with the contact blade(s).

The blade(s) 400 are another key design area which are pivotal to forming reliable, consistent electrical and mechanical connection with the open coil lead. As the actual electrical connection point(s) to the lead, the blade 400 and, more specifically, extension portion 420, must be capable of cutting, pushing or otherwise moving or removing the insulation which covers the conductive wire of the lead. In order to make a connection through the insulation, the tip/terminal edge of each member 421, 422 protruding downward into cavity 204 should have an angle grind, sharpness, or other feature enabling them to cut through the insulation of the lead. Simultaneously, the members 421, 422 and the blade 400 in general do not damage the lead or other elements of the connector 100 (e.g., by cut completely through the conductive wire of the lead, as this would result in a connection that is not reliable or consistent). Notably, although reference is made to two members in this section, it will be understood that one, two, three, or more members can be provided within the blade assembly 400 without departing from the invention.

A number of design aspects of the blade(s) may be modified and optimized to cut through the insulation without severing or cutting through the wire of the lead. For example, the angle(s) at which the members 421, 422 are bent and initiate contact with the lead is significant. Also, the length and/or depth of the cutting edge relative to the depth of the guide channel 213, bottom panel 203, internal cavity 204, or other aspects of the base 200 and/or connector 100 and the sharpness (or bluntness), the rigidity, and/or flexibility of the cutting edge are further examples. Significantly, when multiple extension members and/or cutting edges are present, the foregoing characteristics of the cutting edges can be varied and tuned so that the multiple members cooperate in concert to exert differing levels of force to achieve the end result: consistent electrical and mechanical contact between blade 400 and the lead.

In one non-limiting example, the extension portion 420 initially rises up from the flattened, L-shaped base 410 at an acute angle relative to the base 410 between 45° to 75°, with the each member 421, 422 then bending back to an orthogonal position relative to base 410. Preferably, each member 421, 422 possesses similar or identical bending angles and shapes. The cutting edge formed on the base then has an angle, relative to the base 410, between 35° and 60°, with 45° to 50° being preferred. The overall height of the members 421, 422 is offset by less than 10% and, more preferably, about 6.5%, relative to the height of the longest member, while the terminal edges of the members 421, 422 are spaced apart (in the horizontal direction) by about 15% to 30% of the length of the longest member. This combination of an initial bend (returning to vertical), cutting angle, and offset represents one approach to addressing the challenges noted herein.

Given the multitude of parameters as well as the variable nature of the lead and its exact positioning within the connector 100 (i.e., where the coils exactly line up compared with the blades), it may be advantageous in a preferred embodiment to incorporate two, three or more blades. These may be positioned such that they have variable features, such as bend angle, sharpness, or flexibility but in an ideal embodiment have different lengths and/or be positioned at different depths. This will allow the blade 400 to form increasingly secure connections with the wire of the lead (via the multiple members and their terminal edges) while ensuring that one or more of the blades does not make a connection that over penetrates (i.e., cuts completely through the wire of the lead). As above, the angle, spring force/flexion, height/axial distance, and relative spacing between the contact members can be consistent or varied, with the variations acting in concert to produce the combined effect of establishing and maintaining consistent electrical and mechanical contact without damaging the lead or the connector.

Figure 2E:
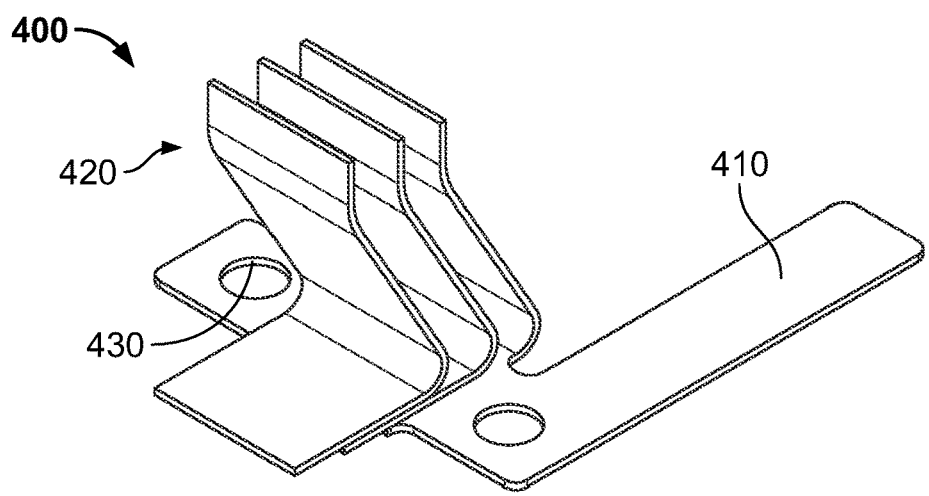
Figure 2F:
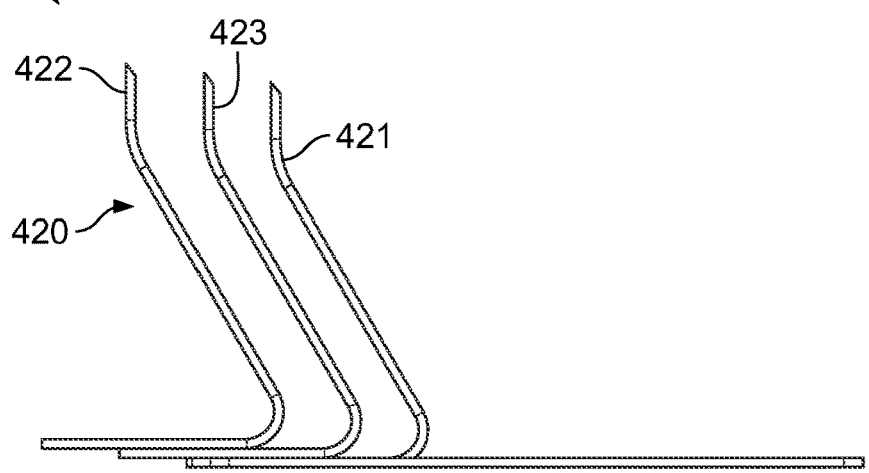

In one embodiment shown in FIGS. 2E and 2F, the connector may incorporate three blades 421, 422, 423, wherein the first blade 421 passes through the insulation, but not through any strands of the wire of the lead, while the second blade 423 passes through some strands of the wire of the lead, and the third blade 422 passes through most or all of the strands of the wire of the lead. The selection of various properties (as described above) of the blades may also be selected so as to allow the blades to aid in guiding the open coil lead to a position that is conducive to forming a connection. That is, a blade with some angle incorporated may be more effective at pushing or moving the coil of the lead during the closing/locking process such that the blade makes contact with the bottom of a coil once the connector is fully closed (while a straight blade may cause a coil to crush over onto itself, resulting in a difficult or inconsistent connection point since the wire does not have the hard backing of the base of the connector to cleanly and consistently support it). Testing of various blade configurations has confirmed that there are optimal and suboptimal design feature combinations that significantly impact the performance, reliability and consistency with which the connector performs.

Figure 2G:
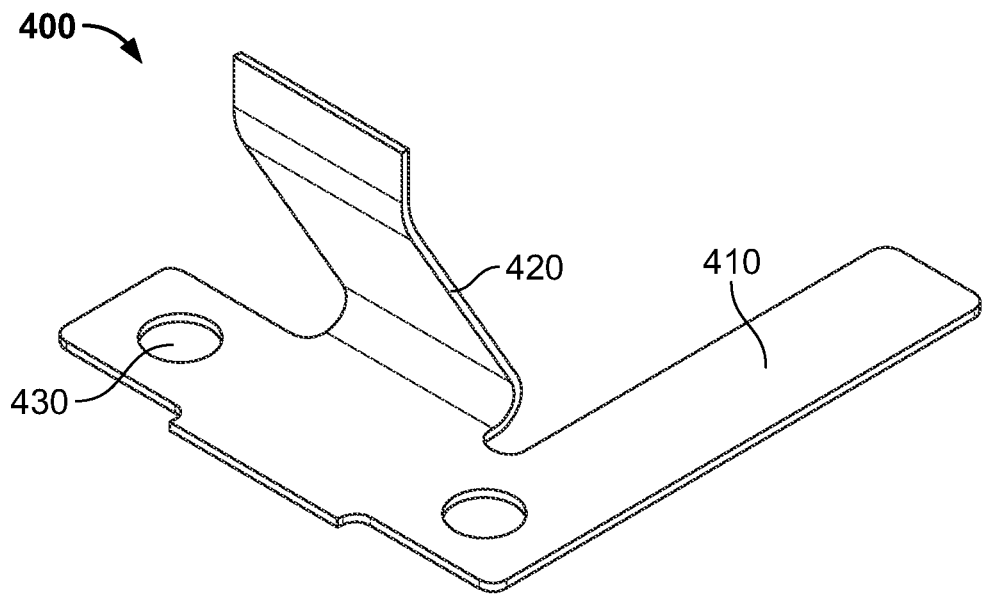
Figure 3A:
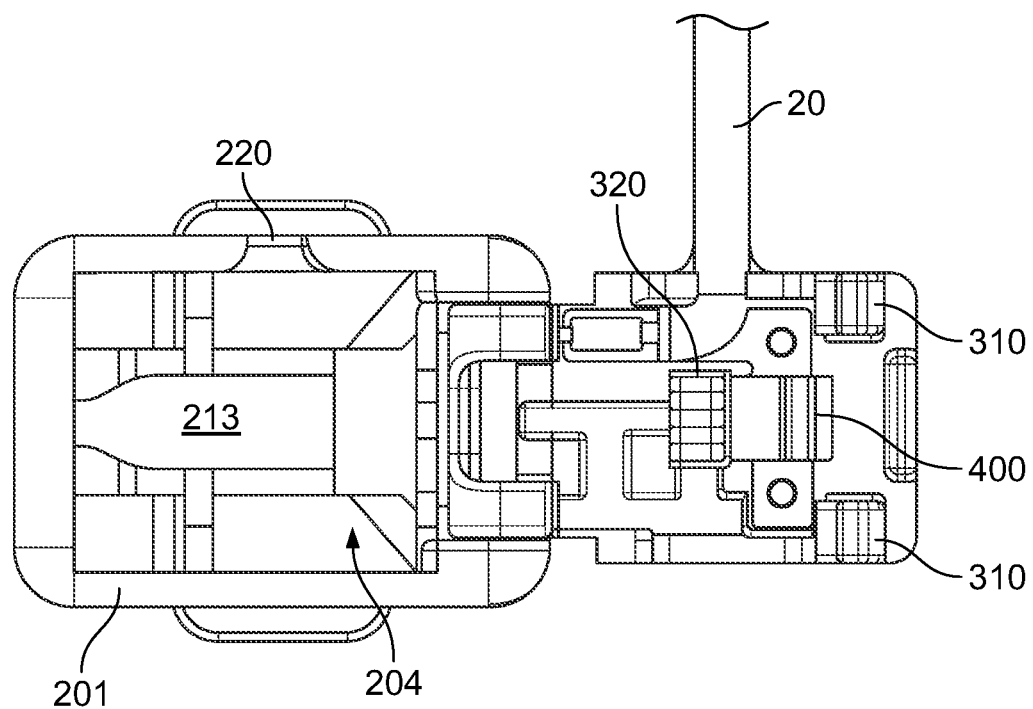
FIG. 3A is a top plan view of FIG. 2A.
Figure 3B:
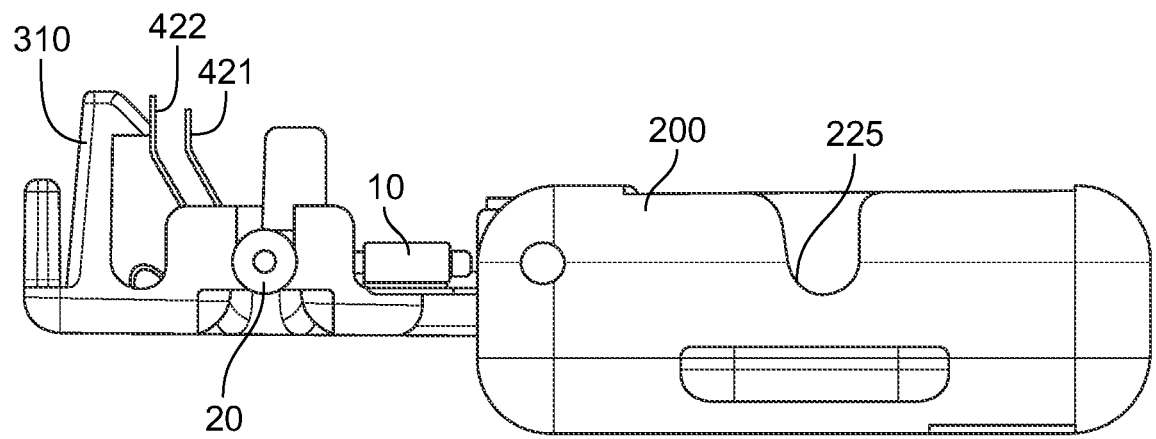
FIG. 3B is a side plan view depicting the funnel-shaped port in which the cable is fed into the lead connector.
Figure 3C:
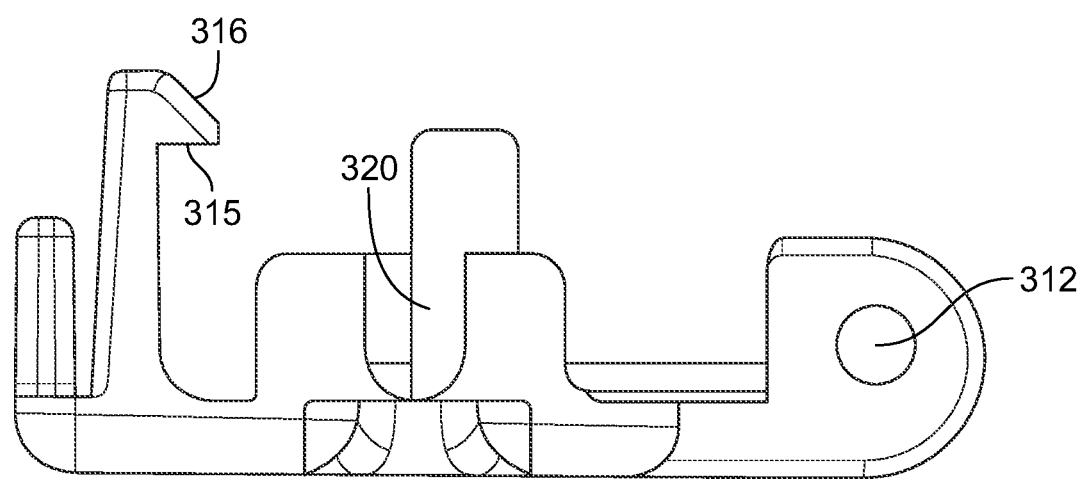
FIG. 3C is an isolated side plan view of the cover of the lead connector shown in FIG. 3A without the extension cable or attachment blade shown (as in FIGS. 3A and 3B).
Figure 4A:
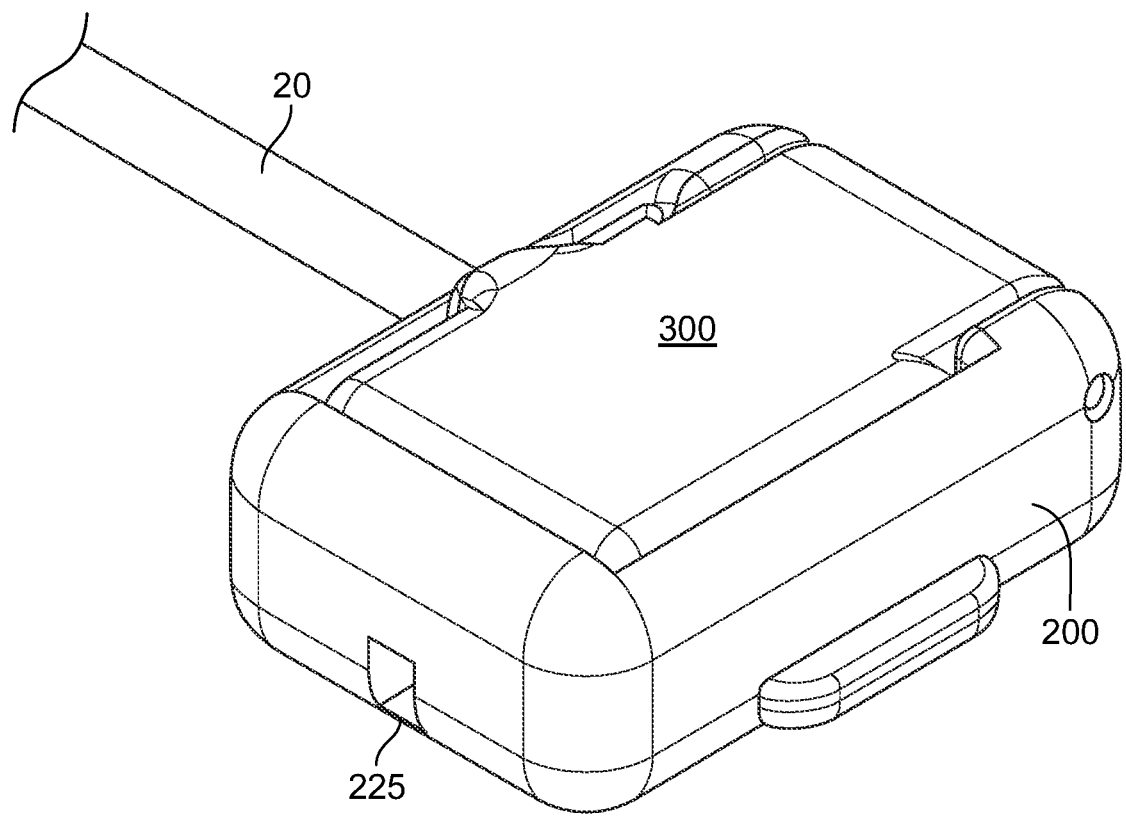
FIGS. 4A and 4B are opposing perspective views showing the lead connector in a fully closed and locked state with the stimulator extension cable and plug attached thereto, but prior to engaging the lead. Note that the plug on the extension cable has been omitted from FIG. 4A.
Figure 4B:
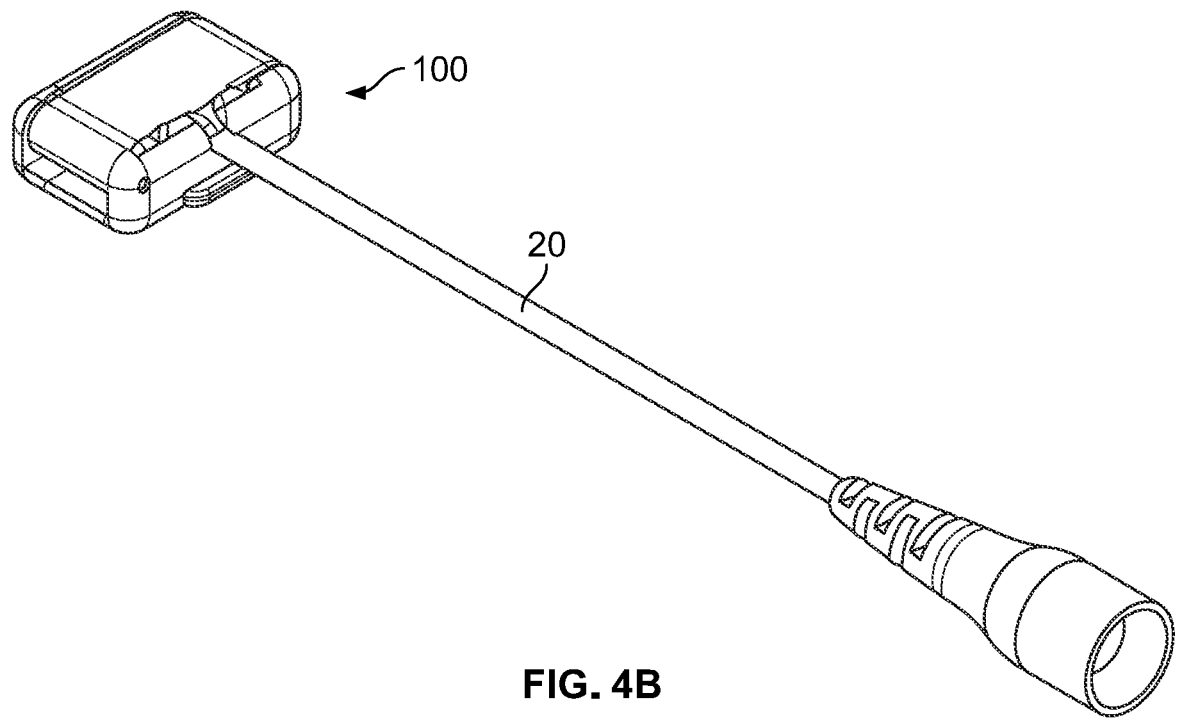
Figure 5A:
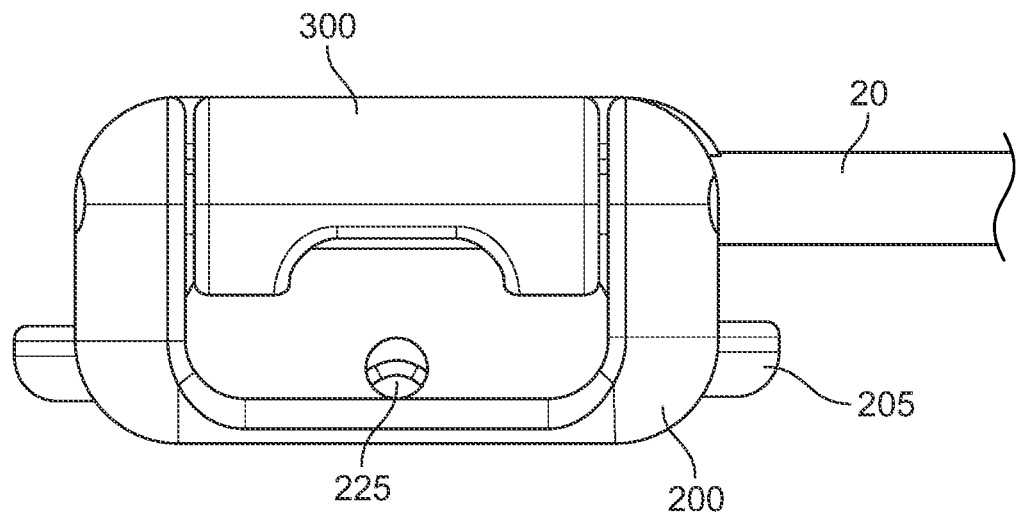
FIGS. 5A through 5D are various plan views of the lead connector in a fully closed, locked state.
Figure 5B:
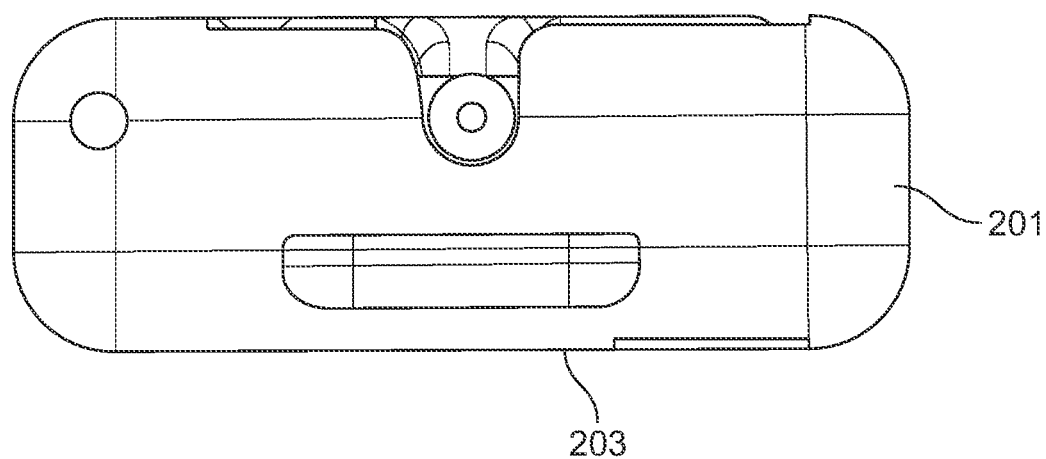
Figure 5C:
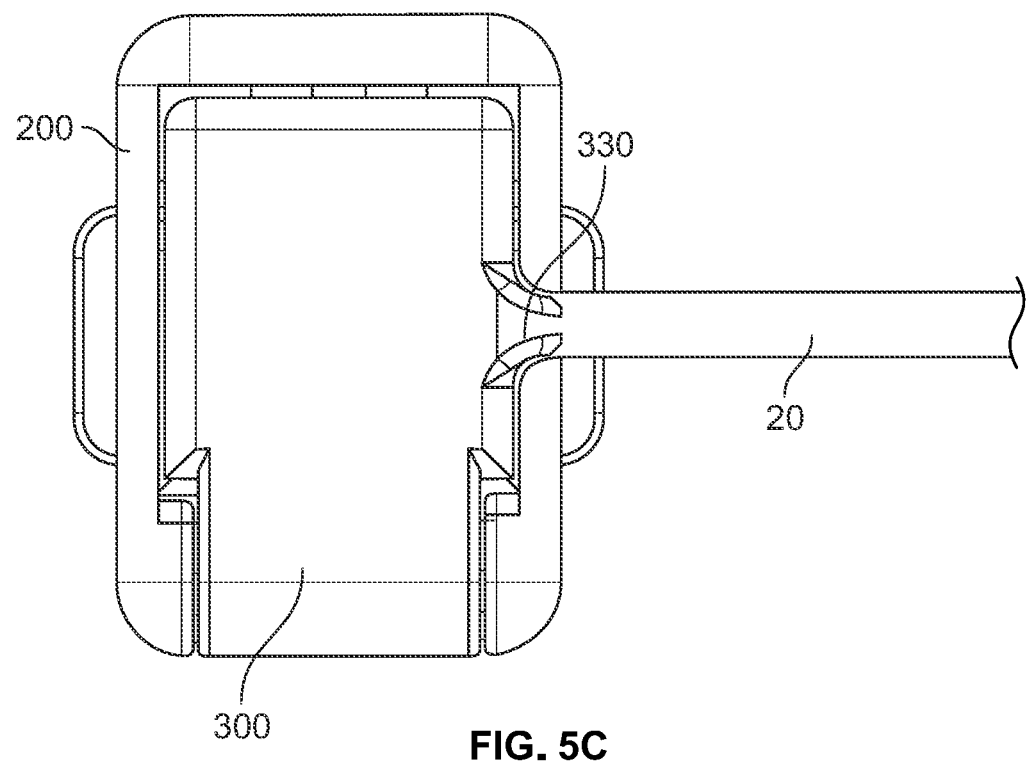
Figure 5D:
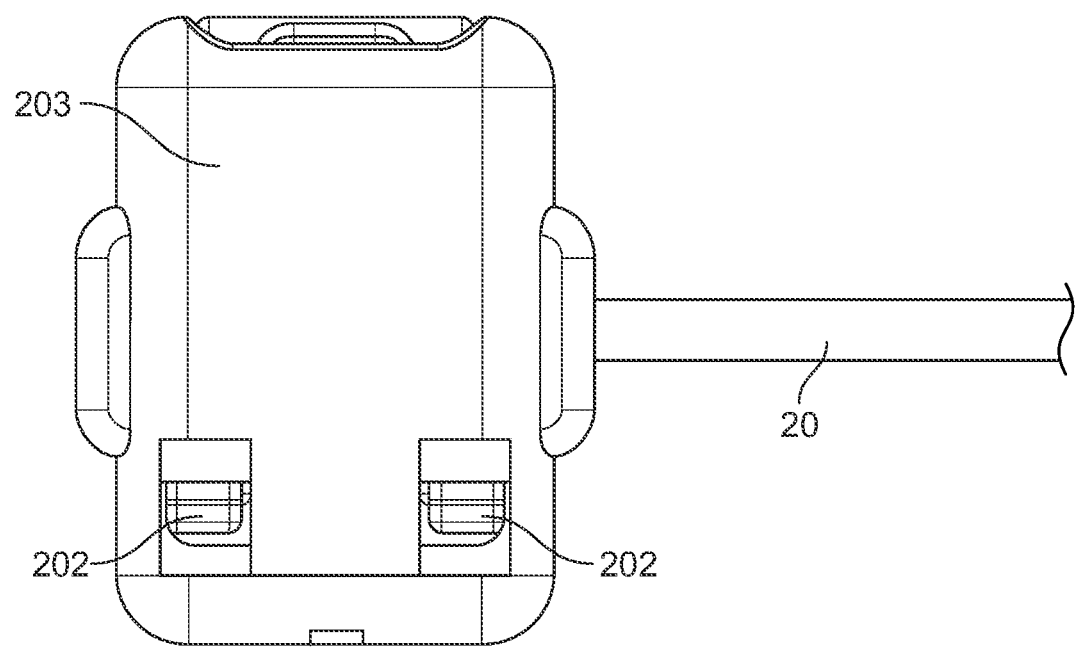

In FIG. 2G, a single blade version is shown. Notably, FIGS. 2D and 2G allow the blade to be formed from a single metallic member, whereas the arrangement in FIGS. 2E and 2F stack a plurality of metallic members one on top of another. Thus, the latter may necessitate welds or some other means of affixing the independent pieces (e.g., bead-and-groove or other snap-fittings, fasteners, etc.) in order to simplify assembly and handling.

When provided in the L-shape with axial extension described above, the base 410 and extension portion 420 of blade 400 conform to the respective location of ports 220, 225 on adjacent sidewalls. That is, cable port 220 is positioned within an elongated sidewall 201 so that the cable 20, upon entering port 220 and being redirected, aligns and makes contact with base 410. Correspondingly, port 225 receives the lead and, when cover 300 is closed but not necessarily locked, extensions 420 cooperate to provide a stripping action to remove insulation from the lead as it comes into contact with members 421, 422. When the cover 300 is locked down, the extension 420 maintains electrical contact with the lead and holds it firmly in place.

Extension 420 may be imparted with resilient and/or biasing force. This type of "springiness" might ensure good contact is maintained with the lead after it has been engaged. Electrically conductive, resilient metals should be used through the entirety of the blade in order to ensure contact. Various grades of stainless steel should be particularly useful in this regard.

Cover 300 has a generally flat, planar shape. One, two, or more support ribs 314 and/or securing post 320 protrude axially downward into the internal cavity 204 when the cover 300 is closed or locked to the base 200. An integral boss 330 is formed along the edge of cover 300 that defines and encloses the port 220 when the cover 300 is closed/locked. Boss 330 provides additional engagement points to hold and secure the cable as it enters the port 220.

Clamps 310 may be provided or integrated with the support ribs 314 as a means of locking the cover 300 to the base 200. Each clamp 310 includes a catchment edge at a distal end of a ramp 316. The catchment edge 315 snap-fits onto catchment 210, while ramp 316 provides a resting position on the catchment 210 to provide the closed but not locked configuration shown in FIGS. 1A through 1E.

Additional features may be incorporated into the base 200 and/or the cover 300 to enable the connector 100 to remain in the resting or "partially ajar" position shown in FIGS. 1A through 1E. This position is desirable because it allows for passage of the lead into and through the connector 100 (i.e., through port 225 and into cavity 204). However, when blade 400 is affixed to the cover 300, this ajar position still allows it to be be snapped closed in order to secure the lead and make the electrical and mechanical connection via the blade 400. Thus, the ajar position limits effort/force required to execute the contact while also reducing the risk of mistakes or wasted time during the lead connection process. Such design features may desirably be incorporated as matching protrusions molded or machined into the structure of the connector lid and base near the hinge of the structure. The features might also include biasing members and/or intergrally formed cams or other rotational stops and grooves formed proximate to the interface between the cover 300 and base 200 so as to correspond to preferred relative positions of the cover 300 and base 200 (i.e., fully open, partially ajar, and/or closed/locked). Thus, when sufficient force is applied, the cover 300 moves from the ajar position with an added-force snapping action (e.g., via biasing member) to urge the cover 300 to lock to the base 200.

Figure 6A:
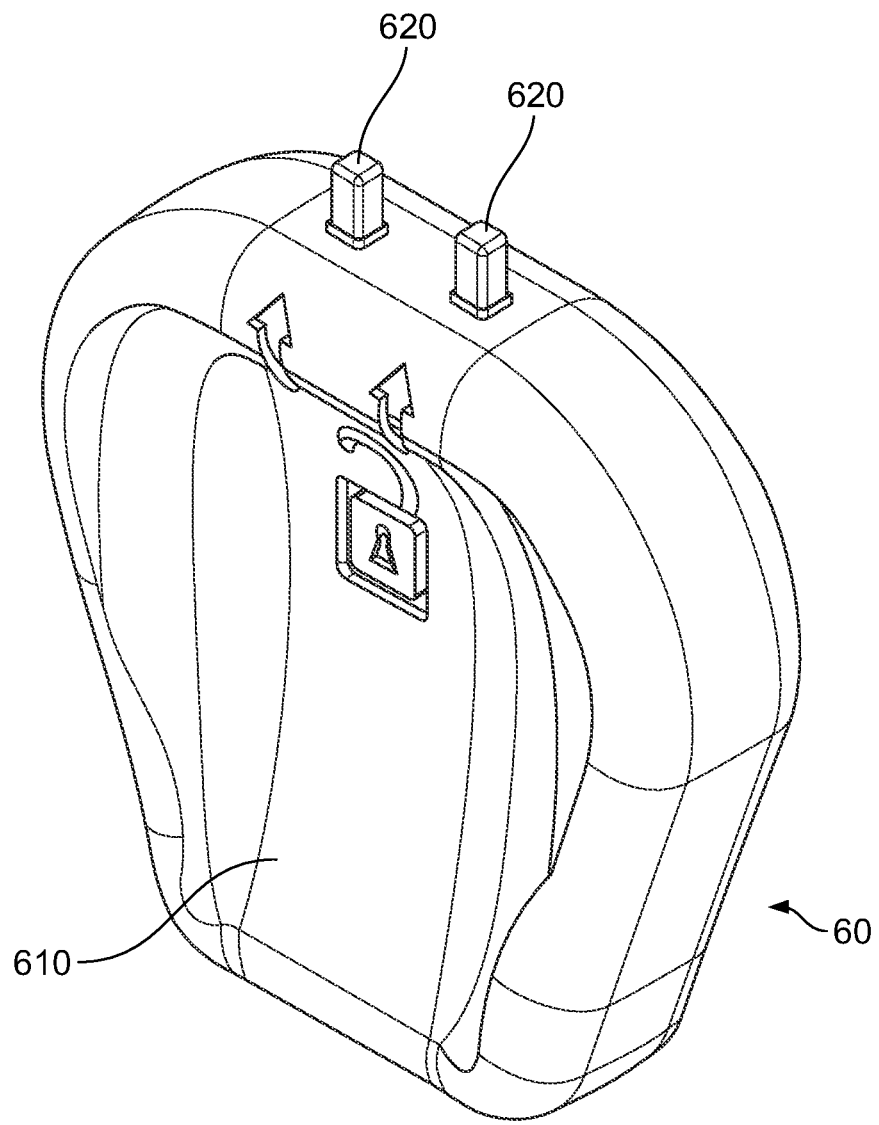
Figure 6B:
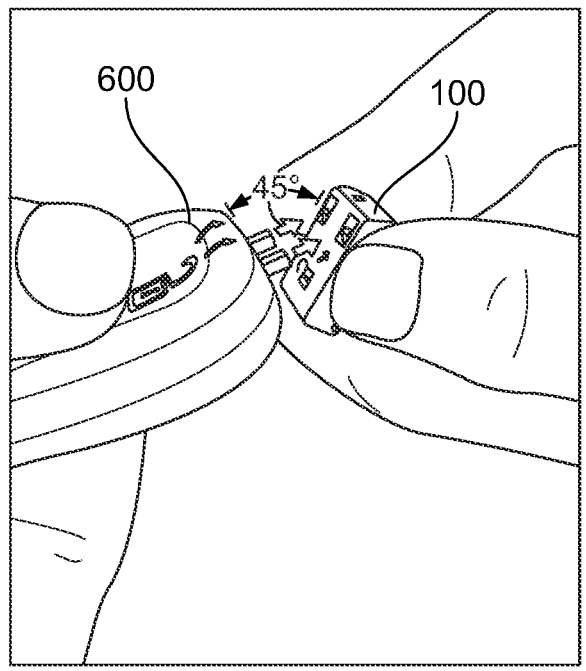
FIG. 6B is a perspective view illustrating how the unlocking device or tool is used in conjunction with the connector.
Figure 7:
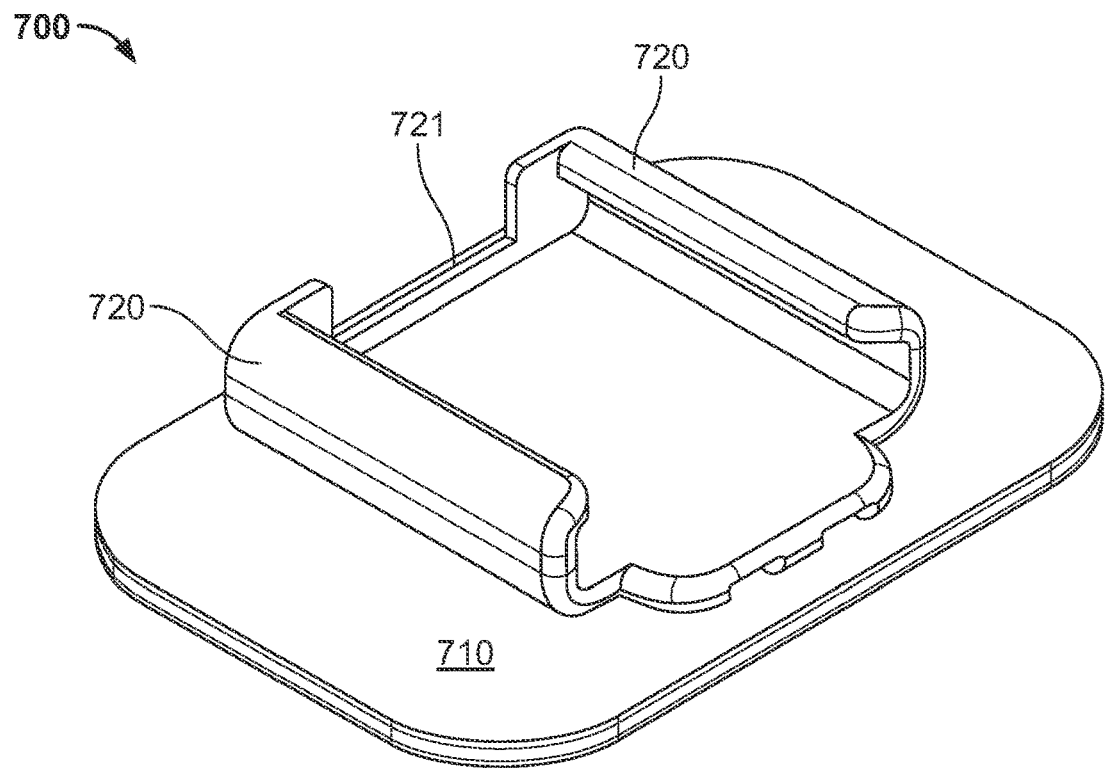
FIG. 7 is a perspective view of a cradle device to stabilize, secure, and hold the lead connector in a desired position.

An unlocking tool 600 can be included in the system. The tool comprises a body member 610 and a pair of protruding bosses 620. Bosses 620 are spaced apart and shaped to be received within the base 200 by way of apertures 202. Bosses 620 are sufficient size and rigidity to dislodge the locking clamps 310 of the cover from cooperating catchments 210 formed within the base cavity 204. While two bosses 620 shown, any number may be employed, so long as they are sized and shaped to cooperate with appropriate apertures 202 and clamps 310. Also, written indicia may be imprinted, stamped, or formed on the body 610 to facilitate use. The use of an unlocking tool or key with the connector may enable the use of a single connector multiple times throughout a procedure, potentially limiting the number of additional components required to go through several stages of a lead testing procedure (for example, connecting to the lead while still within its introducer, being able to unlock and deploy the lead before then reconnecting to the lead with the same connector for use by the patient). FIG. 6B illustrates how tool 600 mates with the connector 100.

The system also embraces a mounting cradle 700, attachable to the patient via an adhesive base 710. A pair of spaced-apart walls 720 are attached to the base 710. The walls 720 receive and secure the connector 100. The walls 720 may be curved or include cooperating features to conform to the connector itself (e.g., via sidewalls 201, cover 300, base 200, etc.). An optional backing wall 721 may partially or completely attach to the opposing side walls 720 to facilitate receipt of the connector and to ensure it remains in place.

Notably, in a preferred embodiment the amount of force required to snap-fit or hold the connector 100 within the cradle 700 should be less than one half the force required to remove the adhesive base/patch 710 from the patient. Features may be provided on the connector 100, including along exterior portions of one or both sidewalls 201, to enable the snap-fit or holding configuration. In one non-limiting example, wings 205 protrude from sidewalls 201 to serve as guides and connection elements on corresponding, conforming portions of walls 720.

With respect to the adhesive base 710, any suitable adhesive material (e.g., those used in bandages and other medical apparatus) can be used on a facing of the base 710, while the walls may be formed integral with base 710. The cradle 700 itself can be formed using a thermosetting polymer(s) (e.g., ABS) capable of withstanding sterilization procedures.

Figure 8:
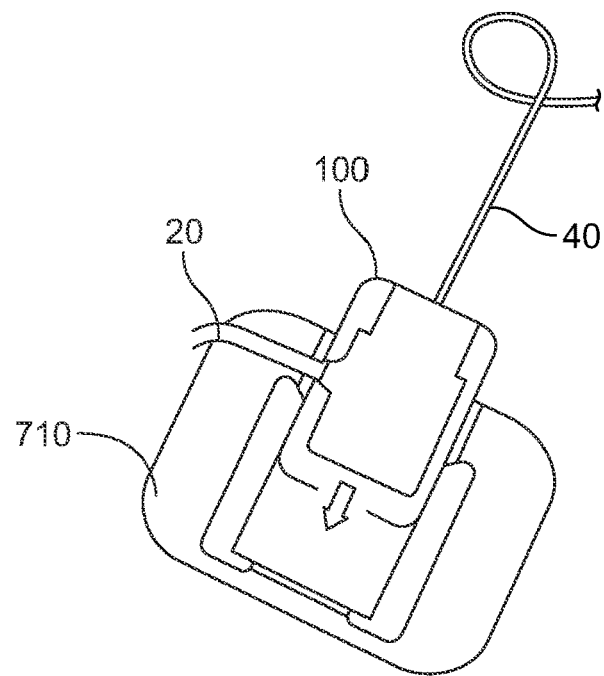
FIG. 8 is a top plan view illustrating how the lead may be fed into the connector when the cover is open or partially ajar.
Figure 9:
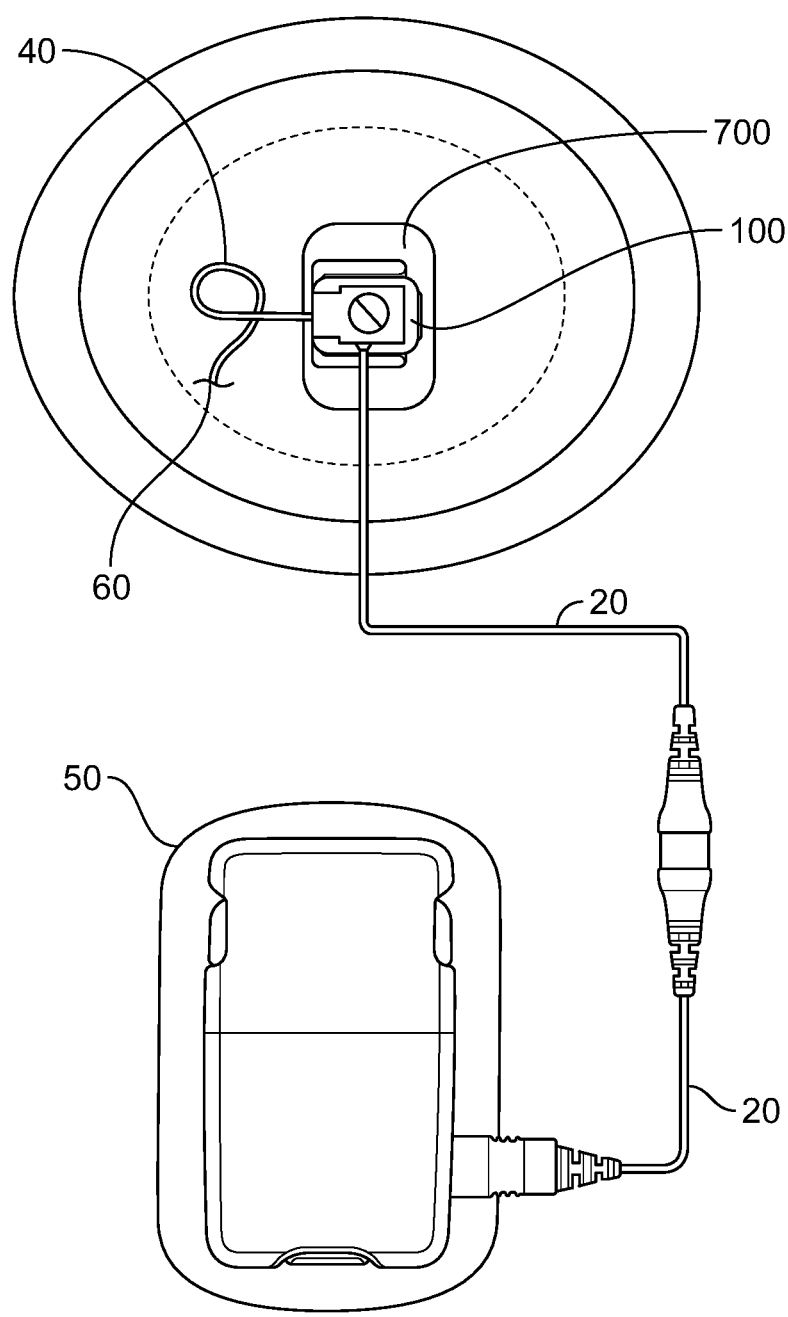
FIG. 9 is a schematic top view of a stimulation system employing the connector seated within a cradle and having multiple extension cables attached to a stimulator device.

FIGS. 8 and 9 provide further context for how the lead 40 may be fed into the connector 100 and, more generally, how the connector 100, cradle 700, and cables 20 integrate with a larger stimulation system. In particular, stimulator 50 is shown, along with lead/electrode insertion point 60 on the patient's body.

Figure 10A:
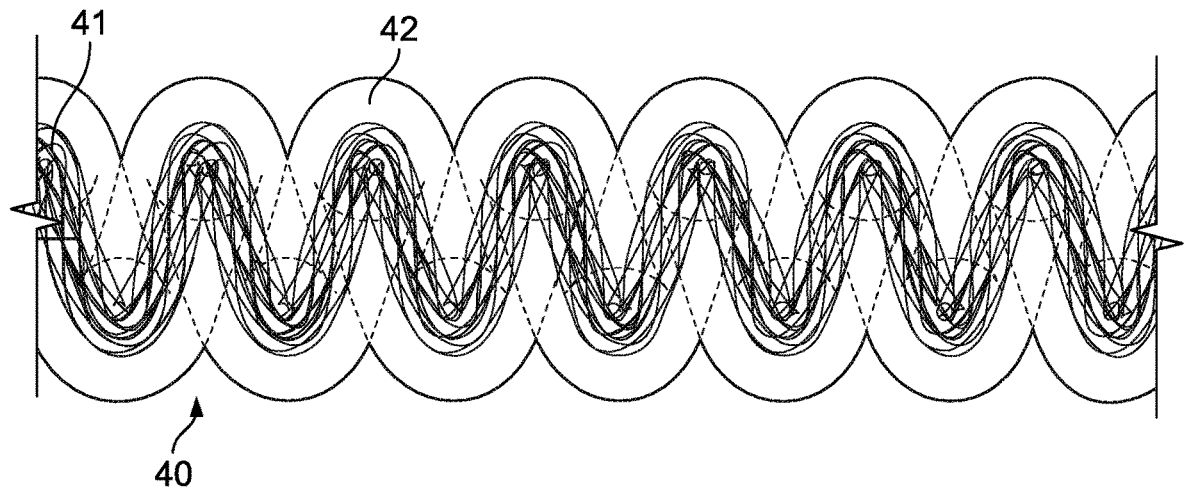
Figure 10B:
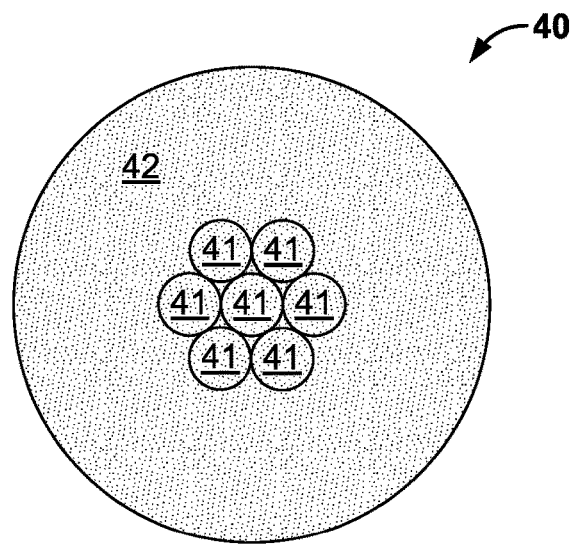
FIG. 10B is a cross sectional, radial view of that same lead.

FIGS. 10A and 10B provide more details with respect to the construction of a lead 40 that is particularly useful with the connector 100. The lead 40 may consist of one or more strands 41 of a conductive material (e.g., stainless steel, silver, copper, etc.) with an insulating coating 42 (e.g., PFA, PTFE, etc.). This insulated lead 40 may be desirably formed into an open coil or helical configuration to provide unique flexibility and infection resistant properties that are desirable for use with stimulation such as but not limited to peripheral nerve stimulation systems.

The connector 100 can be molded or formed from thermosetting polymers (e.g., ABS). Preferably, the material selected is dielectric, strong enough to remain fastened to the ancillary components, and capable of being sterilized.

Figure 11A:
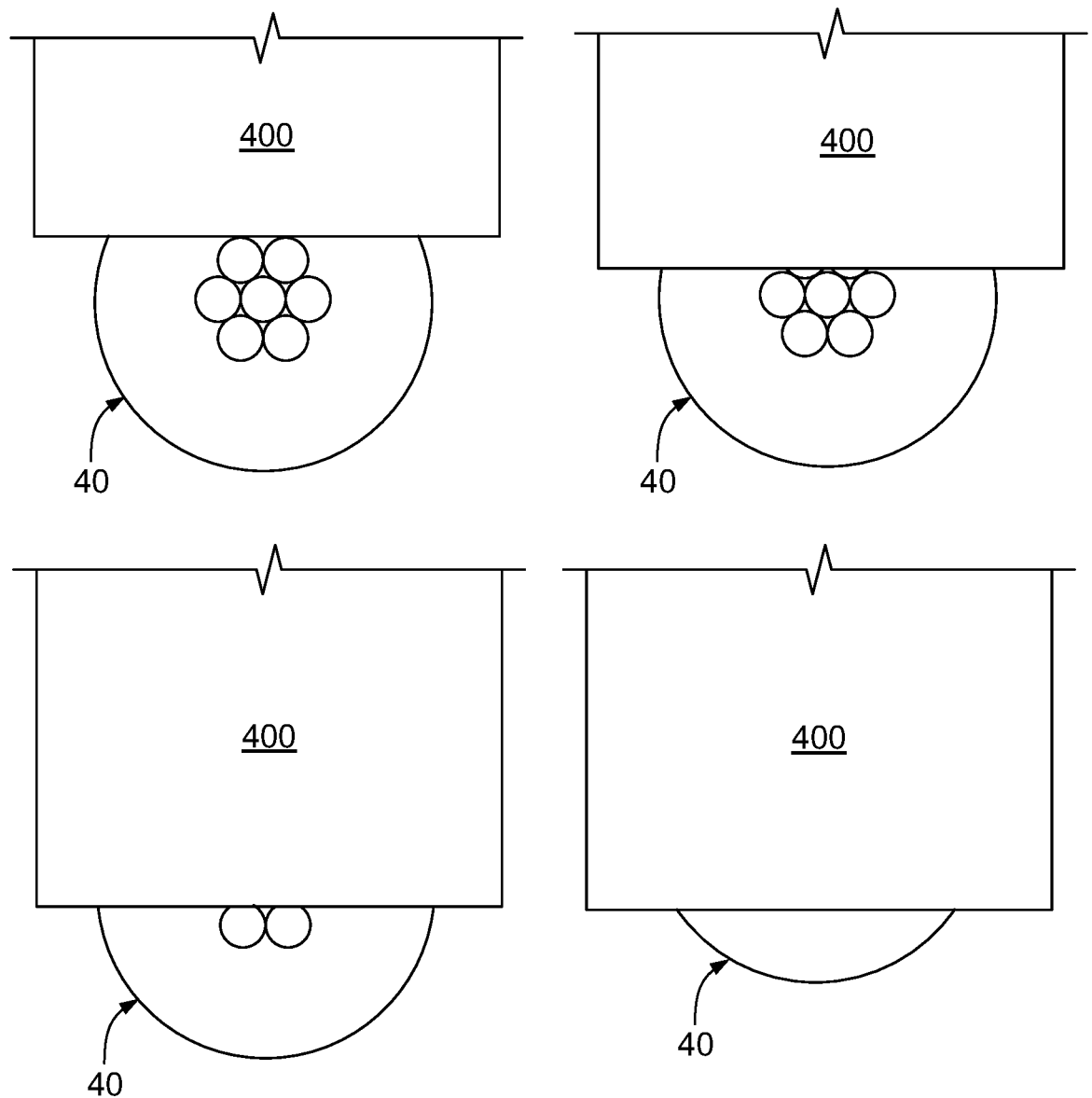
FIGS. 11A and 11B are cross sectional plan views showing the blade as it cuts into a lead.
Figure 11B:
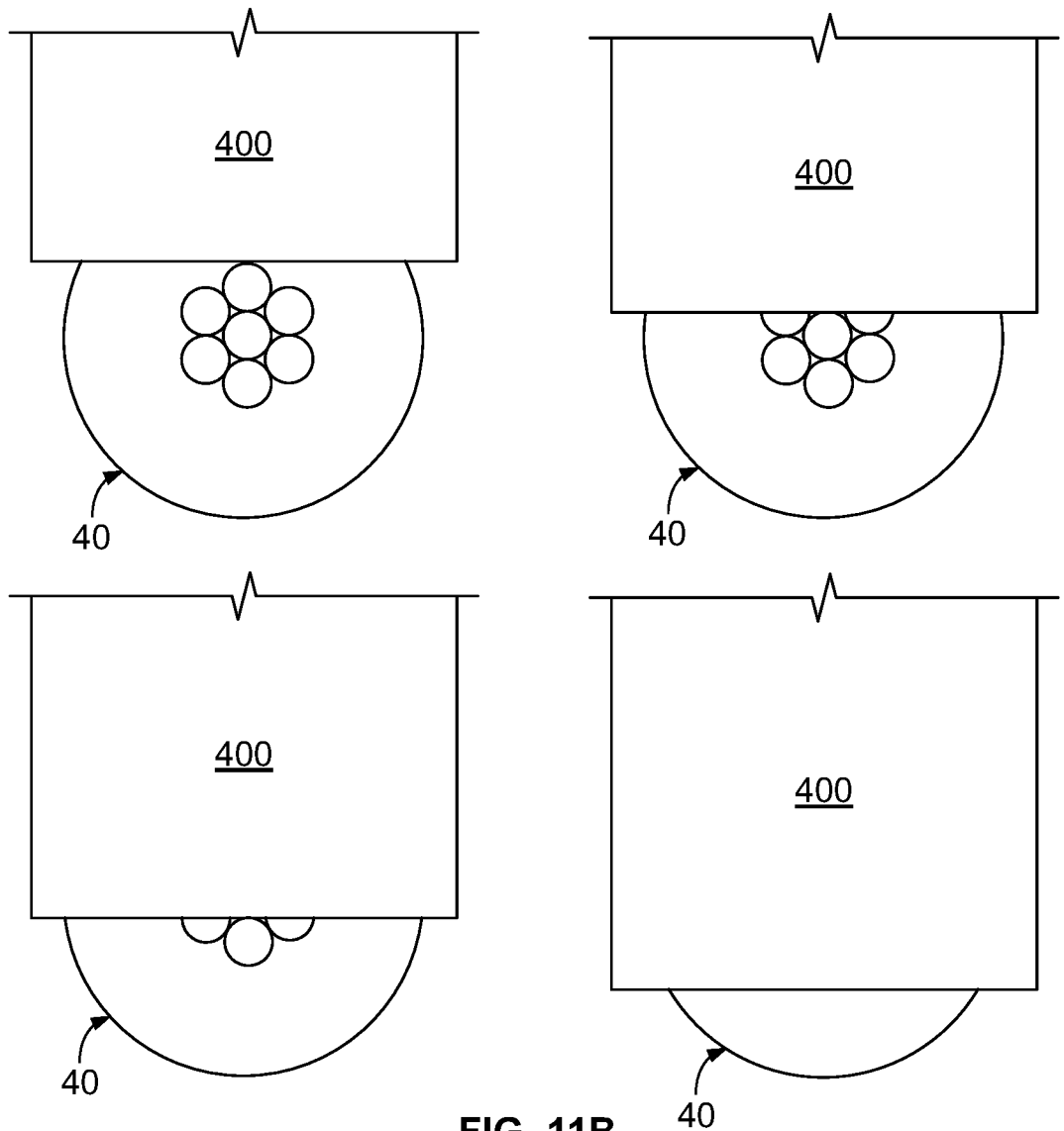
Figure 12:
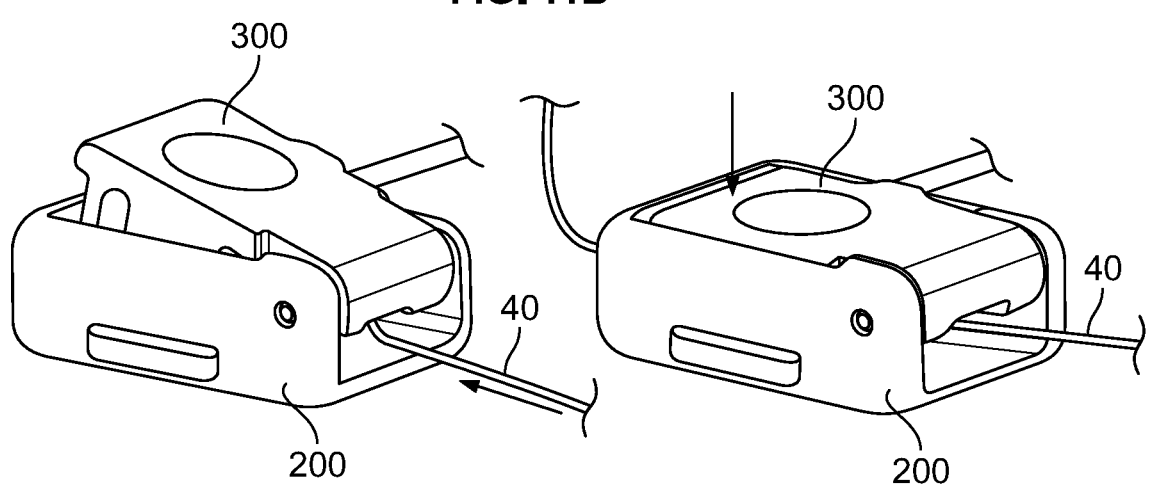
FIG. 12 is a sequential perspective view illustrating how a lead may be inserted through the connector prior to engaging and closing the cover to the base. With reference from left to right, the arrow in the first part of the sequence indicates the direction in which the lead may be inserted, while the arrow in the second part of the sequence represents the force/direction in which the connector may be closed so as to engage the blade assembly with the lead.

FIGS. 11A and 11B illustrate the cutting action of blade 400 through lead 40. The different images in each of these Figures show different depths of cuts through the lead 40, up to and including cutting completely through the conductive portion of the lead 40. In FIG. 11A, the cutting depths achieved by different blades used simultaneously (i.e., two or more blades set apart and/or at different angles so as to simultaneously cut to different depths within the cross sectional radius of the lead 40). While four blades are shown, a similar effect is achieved with any number greater than two. In each case, the combined action of cutting blades ensures there is reliable, consistent contact with the lead wire at multiple redundant points so as to overcome any localized inconsistencies along a single, specific contact point. In some embodiments, the blades which penetrate more deeply into the wire will maintain contact both along the tops of the strands as well as along the cut radius that remains in contact on either of the flat sides of that blade.

FIG. 11B is a time-lapsed illustration of the cutting action of a single blade. Here, it is important to note that the strands 41 are individually severed. Thus, by adjusting the height and/or flexion of the blade 400 and tuning/optimizing it the strength and resiliency of the materials used in the lead 40, it is possible to select a depth of cutting for the blade 400.

Although the embodiments of the present teachings have been illustrated in the accompanying drawings and described in the foregoing detailed description, it is to be understood that the present teachings are not to be limited to just the embodiments disclosed, but that the present teachings described herein is capable of numerous rearrangements, modifications and substitutions without departing from the scope of the claims hereafter.

We claim:

1. A lead connector for an electrical stimulator system, the connector comprising:
   a base having a cable port positioned within a first sidewall and a lead port positioned within a second sidewall;
   a cover, selectively attachable to the base so as to define an internal cavity, the cover having a cable securing boss that is positioned proximate to the cable port when the cover is attached to the base; and
   a contact blade, held between the cover and the base when the cover is attached to the base, the contact blade having a flattened angled portion and an extension portion protruding into the internal cavity so as provide electrical contact between a cable inserted through the cable port and a lead inserted through the lead port, wherein the cover includes a cable boss so that, when the cover is attached to the base, the cable boss encloses a portion of the cable port.

2. The lead connector according to claim 1 wherein the flattened angled portion is L-shaped.

3. The lead connector according to claim 2 wherein the cable is welded to the angled portion.

4. The lead connector according to claim 1 wherein the extension portion includes a plurality of resilient members, with at least one of the plurality of resilient members including a cutting edge at a terminal edge disposed within the internal cavity, said cutting edge stripping or severing the lead when the cover abuts or is attached to the base.

5. The lead connector according to claim 4 wherein the plurality of resilient members consists of two generally parallel members.

6. The lead connector according to claim 5 wherein the two generally parallel members collectively define an S-shape.

7. The lead connector according to claim 5 wherein a first of the two generally parallel members is offset so as to extend into the internal cavity at a different axial height, relative to the flattened angled portion, in comparison to a second of the two generally parallel members.

8. The lead connector according to claim 4 wherein all of the plurality of resilient members each have a cutting edge.

9. The lead connector according to claim 4 wherein the plurality of resilient members includes at least three generally parallel members.

10. The lead connector according to claim 9 wherein all of the parallel members are axially offset relative to one another so as to extend into the internal cavity at a different axial heights relative to the flattened angled portion.

11. The lead connector according to claim 4 wherein the plurality of resilient members have a serpentine shape.

12. The lead connector according to claim 4 wherein the plurality of resilient members form an initial angle, relative to the flattened angled portion of between 45° to 75°.

13. The lead connector according to claim 1 wherein the contact blade is attached to the cover.

14. The lead connector according to claim 1 wherein a hinge connects the cover to the base.

15. The lead connector according to claim 1 wherein the first sidewall is directly adjacent to the second sidewall.

16. The lead connector according to claim 1 wherein the contact blade is metallic.

17. The lead connector according to claim 1 wherein the cover includes an axially-aligned securing post that abuts the base and secures the lead within the internal cavity when the cover is attached to the base.

18. The lead connector according to claim 17 wherein the base includes a guide channel on a bottom panel of the base, the guide channel receiving the lead within the internal cavity.

19. The lead connector according to claim 1 wherein the cover includes at least one ramped clamp and the base includes a cooperating catchment shaped to receive the clamp so that the clamp attaches and locks the cover to the base.

20. A lead connector for an electrical stimulator system, the connector comprising:
   a base having a cable port positioned within a first sidewall and a lead port positioned within a second sidewalk;
   a cover, selectively attachable to the base so as to define an internal cavity, the cover having a cable securing boss that is positioned proximate to the cable port when the cover is attached to the base; and
   a contact blade, held between the cover and the base when the cover is attached to the base, the contact blade having a flattened angled portion and an extension portion protruding into the internal cavity so as provide electrical contact between a cable inserted through the cable port and a lead inserted through the lead port, wherein at least one of the cable port and the lead port has a funnel-shape.

21. A system including the connector of claim 1 further comprising at least one extension cable.

22. The system according to claim 21 wherein a plurality of extension cables connected in series and having a progressively larger diameter relative to the cable received within the cable port.

23. The system according to claim 21 wherein a plurality of extension cables connected in series by way of a magnetic and/or breakaway connection.

24. A system comprising:
   a lead connector for an electrical stimulator system, the connector comprising:
      a base having a cable port positioned within a first sidewall and a lead port positioned within a second sidewall;
      a cover, selectively attachable to the base so as to define an internal cavity, the cover having a cable securing boss that is positioned proximate to the cable port when the cover is attached to the base; and a contact blade, held between the cover and the base when the cover is attached to the base, the contact blade having a flattened angled portion and an extension portion protruding into the internal cavity so as provide electrical contact between a cable inserted through the cable port and a lead inserted through the lead port; and an unlocking tool having a plurality of bosses cooperating with corresponding apertures in the cover or the base to release a clamp that attaches and locks the cover to the base.

25. The system according to claim 24 wherein the cover includes at least one ramped clamp and the base includes a cooperating catchment shaped to receive the clamp so that the clamp attaches and locks the cover to the base and wherein the plurality of bosses release the clamp from the catchment when inserted through the corresponding apertures in the cover.

26. A system comprising:
a lead connector for an electrical stimulator system, the connector comprising:
a base having a cable port positioned within a first sidewall and a lead port positioned within a second sidewalk;
a cover, selectively attachable to the base so as to define an internal cavity, the cover having a cable securing boss that is positioned proximate to the cable port when the cover is attached to the base; and
a contact blade, held between the cover and the base when the cover is attached to the base, the contact blade having a flattened angled portion and an extension portion protruding into the internal cavity so as provide electrical contact between a cable inserted through the cable port and a lead inserted through the lead port; and
a mounting cradle having a pair of side walls sized to receive and secure the connector and a cradle base.

27. The system according to claim 26 wherein the base comprises an adhesive patch.

28. The system according to claim 26 further comprising an end wall connected to the pair of side walls.

29. The system according to claim 26 wherein the connector includes a feature for snap-fitting to the cradle.

30. The system according to claim 29 wherein the feature comprises laterally extending wings on opposing sidewalls of the base of the connector.

* * * * *